(12) United States Patent
Harris et al.

(10) Patent No.: US 10,786,252 B2
(45) Date of Patent: Sep. 29, 2020

(54) SURGICAL STAPLING END EFFECTOR COMPONENT WITH DEFORMABLE TIP HAVING VOID

(71) Applicant: ETHICON LLC, Guaynabo, PR (US)

(72) Inventors: Jason L. Harris, Lebanon, OH (US); Gregory J. Bakos, Mason, OH (US); Chester O. Baxter, III, Loveland, OH (US); Frederick E. Shelton, IV, Hillsboro, OH (US)

(73) Assignee: Ethicon LLC, Guaynabo, PR (US)

( * ) Notice: Subject to any disclaimer, the term of this patent is extended or adjusted under 35 U.S.C. 154(b) by 132 days.

(21) Appl. No.: 16/035,803

(22) Filed: Jul. 16, 2018

(65) Prior Publication Data
US 2020/0015811 A1 Jan. 16, 2020

(51) Int. Cl.
*A61B 17/28* (2006.01)
*A61B 17/072* (2006.01)
(Continued)

(52) U.S. Cl.
CPC .......... *A61B 17/072* (2013.01); *A61B 17/282* (2013.01); *A61B 17/2909* (2013.01);
(Continued)

(58) Field of Classification Search
CPC . A61B 17/072; A61B 17/2909; A61B 17/282; A61B 2017/2946;
(Continued)

(56) References Cited

U.S. PATENT DOCUMENTS 2,679,249 A * 5/1954 Weihmann ............. A61B 17/32
606/174
2,887,111 A * 5/1959 Leyro Diaz .......... A61B 17/282
606/148
(Continued)

FOREIGN PATENT DOCUMENTS

CN 204 931 760 U 1/2016
CN 209 269 768 U 8/2019
(Continued)

OTHER PUBLICATIONS

European Search Report dated Aug. 7, 2018 for Application No. 18157228.0, 8 pages.
(Continued)

*Primary Examiner* — Robert F Long
(74) *Attorney, Agent, or Firm* — Frost Brown Todd LLC

(57) ABSTRACT

An instrument includes a body, a shaft, and an end effector in communication with the shaft. The end effector includes opposing jaws, a staple cartridge, and a placement tip located at a distal end of one of the jaws. The placement tip includes first and second legs extending distally from one of the jaws. A void extends completely through the placement tip and separates the first and second legs. A distal portion connects the first and second legs. The distal portion has a first cross-sectional height that is greater than a second cross-sectional height of the first and second legs. The placement tip may include a body portion formed between an outer perimeter and an inner perimeter. The inner perimeter is defined by a void extending through the placement tip. At least a distal end of the body portion is bent towards the opposing jaw.

20 Claims, 18 Drawing Sheets

(51) Int. Cl.
*A61B 17/29* (2006.01)
*A61B 17/064* (2006.01)

(52) U.S. Cl.
CPC .............. *A61B 2017/0645* (2013.01); *A61B 2017/07221* (2013.01); *A61B 2017/07257* (2013.01); *A61B 2017/07271* (2013.01); *A61B 2017/07285* (2013.01); *A61B 2017/2913* (2013.01); *A61B 2017/2926* (2013.01); *A61B 2017/2946* (2013.01)

(58) Field of Classification Search
CPC .... A61B 2017/2926; A61B 2017/2913; A61B 2017/07285; A61B 2017/07271; A61B 2017/07257; A61B 2017/07221; A61B 2017/0645; A61B 17/07207; A61B 2090/08021; A61B 2017/00964; A61B 2017/00477; A61B 2090/0807; A61B 2017/00946; A61B 2017/07214
USPC ............ 227/175.1-182.1; 606/139, 142, 143
See application file for complete search history.

(56) References Cited

U.S. PATENT DOCUMENTS

| | | | |
|---|---|---|---|
| 4,805,823 A | 2/1989 | Rothfuss | |
| 4,815,465 A * | 3/1989 | Alvarado | A61B 17/128 606/139 |
| 4,944,732 A * | 7/1990 | Russo | A61J 15/0015 604/105 |
| 5,014,899 A | 5/1991 | Presty et al. | |
| 5,071,052 A * | 12/1991 | Rodak | A61B 17/072 227/124 |
| 5,219,354 A * | 6/1993 | Choudhury | A61B 17/0644 606/142 |
| 5,337,937 A * | 8/1994 | Remiszewski | A61B 17/0686 227/182.1 |
| 5,405,072 A * | 4/1995 | Zlock | A61B 17/07207 227/175.1 |
| 5,415,334 A | 5/1995 | Williamson et al. | |
| 5,465,895 A | 11/1995 | Knodel et al. | |
| 5,476,206 A * | 12/1995 | Green | A61B 17/07207 227/176.1 |
| 5,597,107 A | 1/1997 | Knodel et al. | |
| 5,626,595 A * | 5/1997 | Sklar | A61B 17/32001 606/170 |
| 5,632,432 A | 5/1997 | Schulze et al. | |
| 5,673,840 A | 10/1997 | Schulze et al. | |
| 5,704,534 A | 1/1998 | Huitema et al. | |
| 5,728,112 A * | 3/1998 | Yoon | A61B 17/04 606/139 |
| 5,792,135 A | 8/1998 | Madhani et al. | |
| 5,814,055 A | 9/1998 | Knodel et al. | |
| 5,817,084 A | 10/1998 | Jensen | |
| 5,878,193 A | 3/1999 | Wang et al. | |
| 5,919,206 A * | 7/1999 | Gengler | A61B 17/295 606/170 |
| 6,206,823 B1 * | 3/2001 | Kolata | A61B 17/00008 600/127 |
| 6,231,565 B1 | 5/2001 | Tovey et al. | |
| 6,241,740 B1 * | 6/2001 | Davis | A61B 17/1227 606/139 |
| 6,364,888 B1 | 4/2002 | Niemeyer et al. | |
| 6,524,238 B2 * | 2/2003 | Velikaris | A61B 17/02 16/422 |
| 6,783,524 B2 | 8/2004 | Anderson et al. | |
| 6,978,921 B2 | 12/2005 | Shelton et al. | |
| 7,000,818 B2 | 2/2006 | Shelton et al. | |
| 7,143,923 B2 | 12/2006 | Shelton et al. | |
| 7,303,108 B2 | 12/2007 | Shelton | |
| 7,367,485 B2 | 5/2008 | Shelton et al. | |
| 7,380,695 B2 | 6/2008 | Doll et al. | |
| 7,380,696 B2 | 6/2008 | Shelton et al. | |
| 7,404,508 B2 | 7/2008 | Smith et al. | |
| 7,434,715 B2 | 10/2008 | Shelton et al. | |
| 7,524,320 B2 | 4/2009 | Tierney et al. | |
| 7,644,848 B2 | 1/2010 | Swayze et al. | |
| 7,691,098 B2 | 4/2010 | Wallace et al. | |
| 7,721,930 B2 | 5/2010 | McKenna et al. | |
| 7,806,891 B2 | 10/2010 | Nowlin et al. | |
| 8,066,166 B2 | 11/2011 | Demmy et al. | |
| 8,136,711 B2 | 3/2012 | Beardsley et al. | |
| 8,210,411 B2 | 7/2012 | Yates et al. | |
| 8,348,123 B2 | 1/2013 | Scirica et al. | |
| 8,403,195 B2 | 3/2013 | Beardsley et al. | |
| 8,403,196 B2 | 3/2013 | Beardsley et al. | |
| 8,408,439 B2 | 4/2013 | Huang et al. | |
| 8,453,914 B2 | 6/2013 | Laurent et al. | |
| 8,479,969 B2 | 7/2013 | Shelton | |
| 8,496,153 B2 | 7/2013 | Demmy et al. | |
| 8,573,461 B2 | 11/2013 | Shelton et al. | |
| 8,573,465 B2 | 11/2013 | Shelton | |
| 8,602,288 B2 | 12/2013 | Shelton et al. | |
| 8,616,431 B2 | 12/2013 | Timm et al. | |
| 8,690,039 B2 | 4/2014 | Beardsley et al. | |
| 8,714,429 B2 | 5/2014 | Demmy | |
| 8,771,173 B2 * | 7/2014 | Fonger | A61B 1/32 600/106 |
| 8,783,541 B2 | 7/2014 | Shelton et al. | |
| 8,800,838 B2 | 8/2014 | Shelton | |
| 8,820,605 B2 | 9/2014 | Shelton | |
| 8,844,789 B2 | 9/2014 | Shelton et al. | |
| 8,844,790 B2 | 9/2014 | Demmy et al. | |
| 9,016,546 B2 | 4/2015 | Demmy et al. | |
| 9,039,736 B2 | 5/2015 | Scirica et al. | |
| 9,186,142 B2 | 11/2015 | Fanelli et al. | |
| 9,301,759 B2 | 4/2016 | Spivey et al. | |
| 9,333,003 B2 * | 5/2016 | Kappel | A61B 17/29 |
| 9,433,416 B2 | 9/2016 | Beardsley et al. | |
| 9,517,065 B2 | 12/2016 | Simms et al. | |
| 9,522,004 B2 | 12/2016 | Demmy | |
| 9,597,078 B2 | 3/2017 | Scirica et al. | |
| 9,622,746 B2 | 4/2017 | Simms et al. | |
| 9,713,470 B2 | 7/2017 | Scirica et al. | |
| 9,717,497 B2 | 8/2017 | Zerkle et al. | |
| 9,795,379 B2 | 10/2017 | Leimbach et al. | |
| 9,808,248 B2 | 11/2017 | Hoffman | |
| 9,839,421 B2 | 12/2017 | Zerkle et al. | |
| 9,913,642 B2 | 3/2018 | Leimbach et al. | |
| 9,936,968 B2 | 4/2018 | Demmy et al. | |
| 9,943,311 B2 | 4/2018 | Scirica et al. | |
| 10,080,564 B2 | 9/2018 | Beardsley et al. | |
| 10,166,023 B2 | 1/2019 | Vendely et al. | |
| 2002/0002379 A1 * | 1/2002 | Bishop | A61B 17/32009 606/169 |
| 2004/0243151 A1 | 12/2004 | Demmy et al. | |
| 2005/0119669 A1 * | 6/2005 | Demmy | A61B 17/07207 606/139 |
| 2005/0216055 A1 | 9/2005 | Scirica et al. | |
| 2008/0237297 A1 * | 10/2008 | Demmy | A61B 17/07207 227/176.1 |
| 2008/0269793 A1 * | 10/2008 | Scirica | A61B 17/07207 606/190 |
| 2009/0069806 A1 * | 3/2009 | De La Mora Levy | A61B 17/221 606/46 |
| 2009/0084825 A1 * | 4/2009 | Larson | A61B 17/24 227/176.1 |
| 2010/0213240 A1 * | 8/2010 | Kostrzewski | A61B 17/072 227/180.1 |
| 2013/0112729 A1 * | 5/2013 | Beardsley | A61B 17/07207 227/175.1 |
| 2014/0166723 A1 | 6/2014 | Beardsley et al. | |
| 2014/0239036 A1 | 8/2014 | Zerkle et al. | |
| 2014/0239037 A1 | 8/2014 | Boudreaux et al. | |
| 2014/0239038 A1 | 8/2014 | Leimbach et al. | |
| 2014/0239041 A1 | 8/2014 | Zerkle | |
| 2014/0239043 A1 | 8/2014 | Simms et al. | |
| 2014/0239044 A1 | 8/2014 | Hoffman | |
| 2015/0173752 A1 | 6/2015 | Demmy et al. | |
| 2015/0272575 A1 | 10/2015 | Leimbach et al. | |

(56) References Cited

U.S. PATENT DOCUMENTS

| | | |
|---|---|---|
| 2015/0282809 A1 | 10/2015 | Shelton, IV et al. |
| 2016/0143659 A1 | 5/2016 | Glutz et al. |
| 2016/0278774 A1 | 9/2016 | Shelton, IV et al. |
| 2017/0055981 A1 | 3/2017 | Vendely et al. |
| 2017/0086823 A1 | 3/2017 | Leimbach et al. |
| 2017/0128070 A1* | 5/2017 | Scirica ............. A61B 17/07207 |
| 2018/0235609 A1 | 8/2018 | Harris et al. |
| 2018/0235610 A1 | 8/2018 | Harris et al. |
| 2018/0235611 A1 | 8/2018 | Harris et al. |
| 2018/0235619 A1 | 8/2018 | Harris et al. |
| 2018/0325514 A1 | 11/2018 | Harris et al. |
| 2018/0325515 A1 | 11/2018 | Harris et al. |
| 2018/0325516 A1 | 11/2018 | Harris et al. |

FOREIGN PATENT DOCUMENTS

| | | |
|---|---|---|
| EP | 1 943 960 A2 | 7/2008 |
| EP | 2 165 656 A2 | 3/2010 |
| EP | 2 772 203 A2 | 9/2014 |
| EP | 2772202 | 9/2014 |
| EP | 2 783 642 A1 | 10/2014 |
| EP | 2 898 839 A1 | 7/2015 |
| EP | 3 363 385 A1 | 8/2018 |
| EP | 3 420 936 A1 | 1/2019 |
| WO | WO 2004/096057 | 11/2004 |
| WO | WO 2017/083129 | 5/2017 |

OTHER PUBLICATIONS

International Search Report and Written Opinion dated Apr. 19, 2018 for International Application No. PCT/US2018/017751, 17 pages.
U.S. Appl. No. 60/466,378, filed Apr. 29, 2003.
U.S. Appl. No. 60/843,254, filed Sep. 8, 2006.
U.S. Appl. No. 11/851,495, filed Sep. 7, 2007.
U.S. Appl. No. 14/868,718, filed Sep. 29, 2015.
U.S. Appl. No. 15/435,573, filed Feb. 17, 2017.
U.S. Appl. No. 15/435,607, filed Feb. 17, 2017.
U.S. Appl. No. 15/435,618, filed Feb. 17, 2017.
U.S. Appl. No. 15/435,631, filed Feb. 17, 2017.
U.S. Appl. No. 16/035,821, filed Jul. 16, 2018.
U.S. Appl. No. 16/035,825, filed Jul. 16, 2018.
U.S. Appl. No. 16/035,831, filed Jul. 16, 2018.
U.S. Appl. No. 16/035,834, filed Jul. 16, 2018.
U.S. Appl. No. 16/035,856, filed Jul. 16, 2018.
U.S. Appl. No. 16/035,860, filed Jul. 16, 2018.
U.S. Appl. No. 16/035,865, filed Jul. 16, 2018.
U.S. Appl. No. 16/035,872, filed Jul. 16, 2018.
Design U.S. Appl. No. 29/594,332, filed Feb. 17, 2017.
Design U.S. Appl. No. 29/594,335, filed Feb. 17, 2017.
Design U.S. Appl. No. 29/594,340, filed Feb. 17, 2017.
European Search Report, Partial, and Provisional Written Opinion dated Dec. 17, 2019 for Application No. EP 19186251.5, 21 pgs.
International Search Report and Written Opinion dated Feb. 11, 2020 for Application No. PCT/IB2019/056036, 22 pgs.

\* cited by examiner

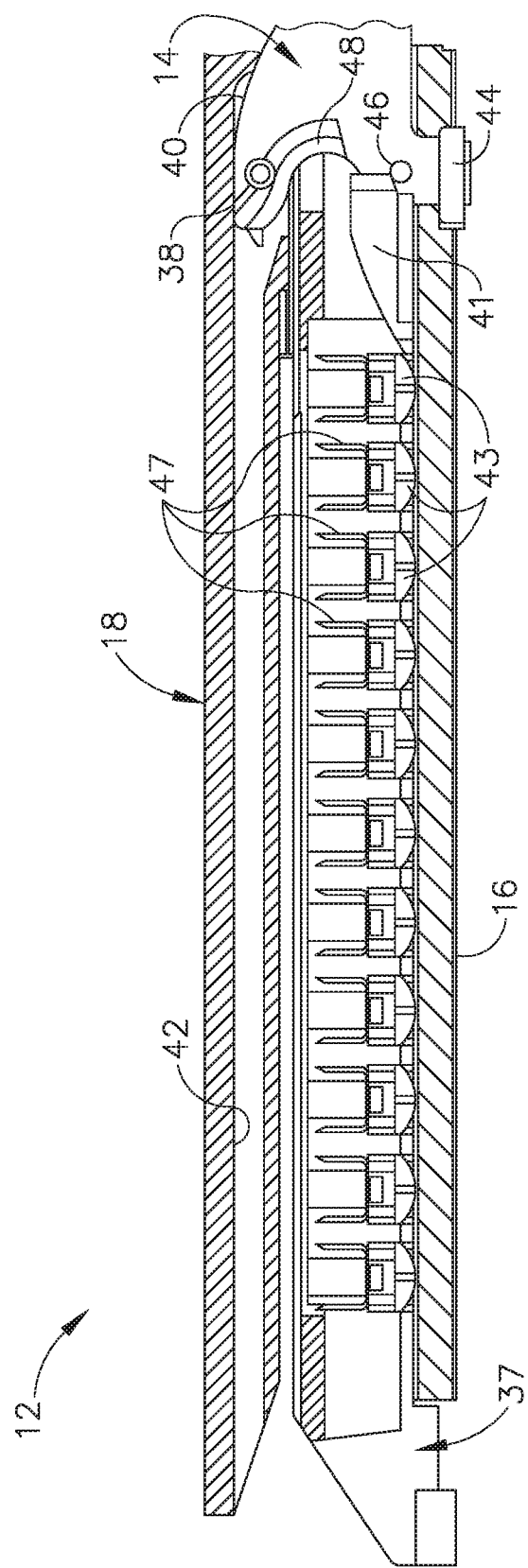

SURGICAL STAPLING END EFFECTOR COMPONENT WITH DEFORMABLE TIP HAVING VOID

BACKGROUND

Endoscopic surgical instruments may include a shaft between the end effector and a handle portion, which is manipulated by the clinician. Such a shaft may enable insertion through a trocar to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 7,380,696, entitled "Articulating Surgical Stapling Instrument Incorporating a Two-Piece E-Beam Firing Mechanism," issued Jun. 3, 2008; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. patents and U.S. patent Publications is incorporated by reference herein.

Surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. For instance, the vessels leading to an organ may be severed and closed by a stapler before removal of the organ from the thoracic cavity. Of course, surgical staplers may be used in various other settings and procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 4A depicts a side cross-sectional view of the end effector of FIG. 3, taken along line 4-4 of FIG. 3, with the firing beam in a proximal position;

Figure 1:
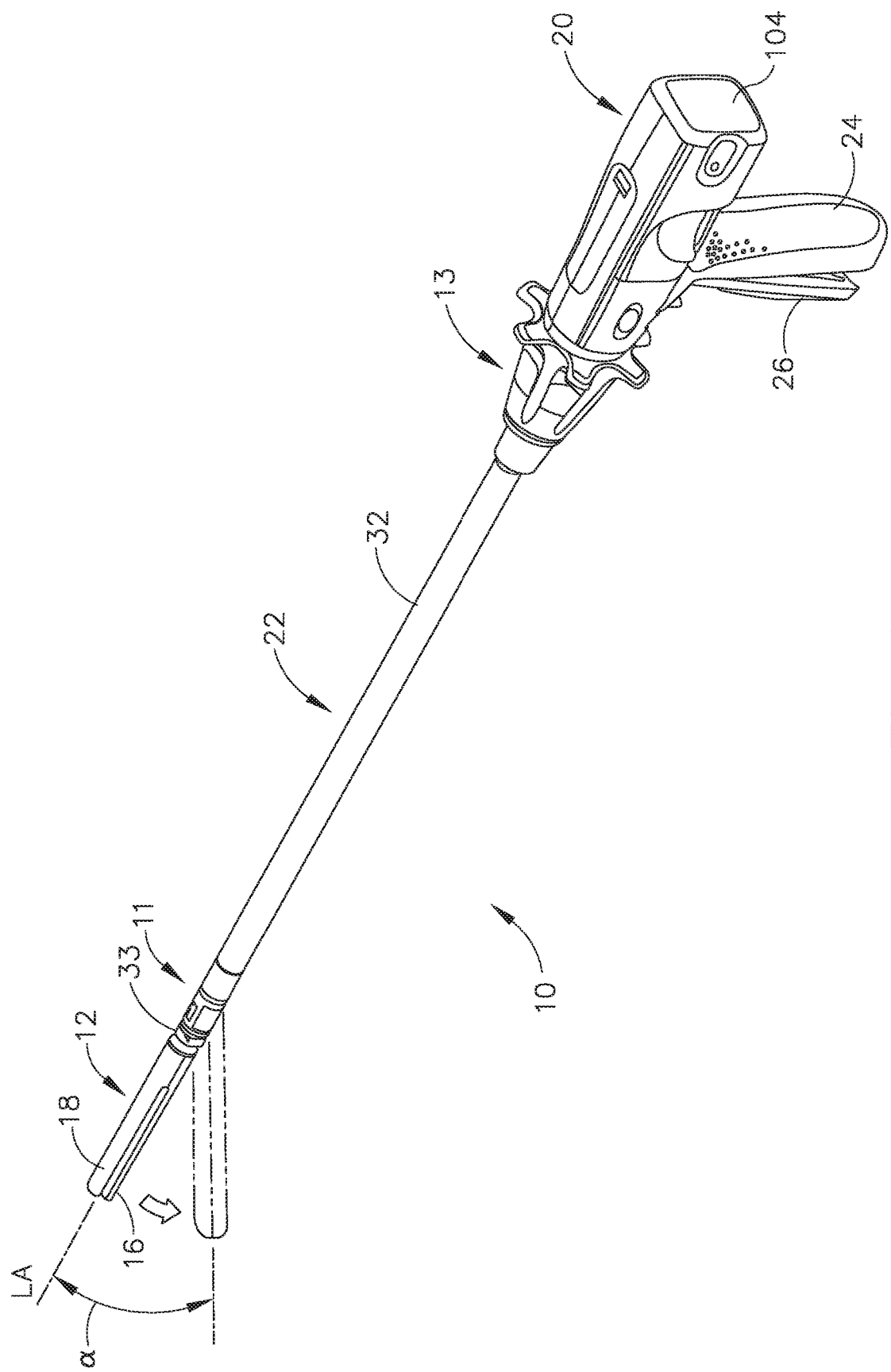
FIG. 1 depicts a perspective view of a first exemplary surgical stapling instrument.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "upper," "lower," "lateral," "transverse," "bottom," "top," are relative terms to provide additional clarity to the figure descriptions provided below. The terms "upper," "lower," "lateral," "transverse," "bottom," "top," are thus not intended to unnecessarily limit the invention described herein.

In addition, the terms "first" and "second" are used herein to distinguish one or more portions of the surgical instrument. For example, a first assembly and a second assembly may be alternatively and respectively described as a second assembly and a first assembly. The terms "first" and "second" and other numerical designations are merely exemplary of such terminology and are not intended to unnecessarily limit the invention described herein.

I. First Exemplary Surgical Instrument Having a First Exemplary End Effector

FIGS. 1-7 depict a first exemplary surgical stapling and severing instrument (10) that is sized for insertion through a trocar cannula or an incision (e.g., thoracotomy, etc.) to a surgical site in a patient for performing a surgical procedure. Instrument (10) of the present example includes a handle portion (20) connected to a shaft (22), which distally terminates in an articulation joint (11), which is further coupled with a first exemplary end effector (12). Shaft (22) may be constructed in accordance with at least some of the teachings of U.S. Pat. No. 9,795,379, entitled "Surgical Instrument with Multi-Diameter Shaft," issued Oct. 24, 2017, the disclosure of which is incorporated by reference herein.

Once articulation joint (11) and end effector (12) are inserted through the cannula passageway of a trocar, articulation joint (11) may be remotely articulated, as depicted in phantom in FIG. 1, by an articulation control (13), such that end effector (12) may be deflected from the longitudinal axis (LA) of shaft (22) at a desired angle (α). Articulation joint (11) and/or articulation control (13) may be constructed and operable in accordance with at least some of the teachings of U.S. Pat. No. 9,186,142, entitled "Surgical Instrument End Effector Articulation Drive with Pinion and Opposing Racks," issued on Nov. 17, 2015, the disclosure of which is incorporated by reference herein; and/or U.S. Pat. No. 9,795,379, the disclosure of which is incorporated by reference herein.

End effector (12) of the present example includes a lower jaw (16) and a pivotable anvil (18). Lower jaw (16) may be constructed in accordance with at least some of the teachings of U.S. Pat. No. 9,808,248, entitled "Installation Features for Surgical Instrument End Effector Cartridge," issued Nov. 7, 2017, the disclosure of which is incorporated by reference herein. Anvil (18) may be constructed in accordance with at least some of the teachings of U.S. Pat. No. 9,517,065, entitled "Integrated Tissue Positioning and Jaw Alignment Features for Surgical Stapler," issued Dec. 13, 2016, the disclosure of which is incorporated by reference herein; U.S. Pat. No. 9,839,421, entitled "Jaw Closure Feature for End Effector of Surgical Instrument," issued Dec. 12, 2017, the disclosure of which is incorporated by reference herein; and/or U.S. Pub. No. 2014/0239037, entitled "Staple Forming Features for Surgical Stapling Instrument," published on Aug. 28, 2014, issued as U.S. Pat. No. 10,092,292 on Oct. 9, 2018, the disclosure of which is incorporated by reference herein.

Handle portion (20) includes a pistol grip (24) and a closure trigger (26). Closure trigger (26) is pivotable toward pistol grip (24) to cause clamping, or closing, of the anvil (18) toward lower jaw (16) of end effector (12). Such closing of anvil (18) is provided through a closure tube (32) and a closure ring (33), which both longitudinally translate relative to handle portion (20) in response to pivoting of closure trigger (26) relative to pistol grip (24). Closure tube (32) extends along the length of shaft (22); and closure ring (33) is positioned distal to articulation joint (11). Articulation joint (11) is operable to communicate/transmit longitudinal movement from closure tube (32) to closure ring (33).

Figure 2:
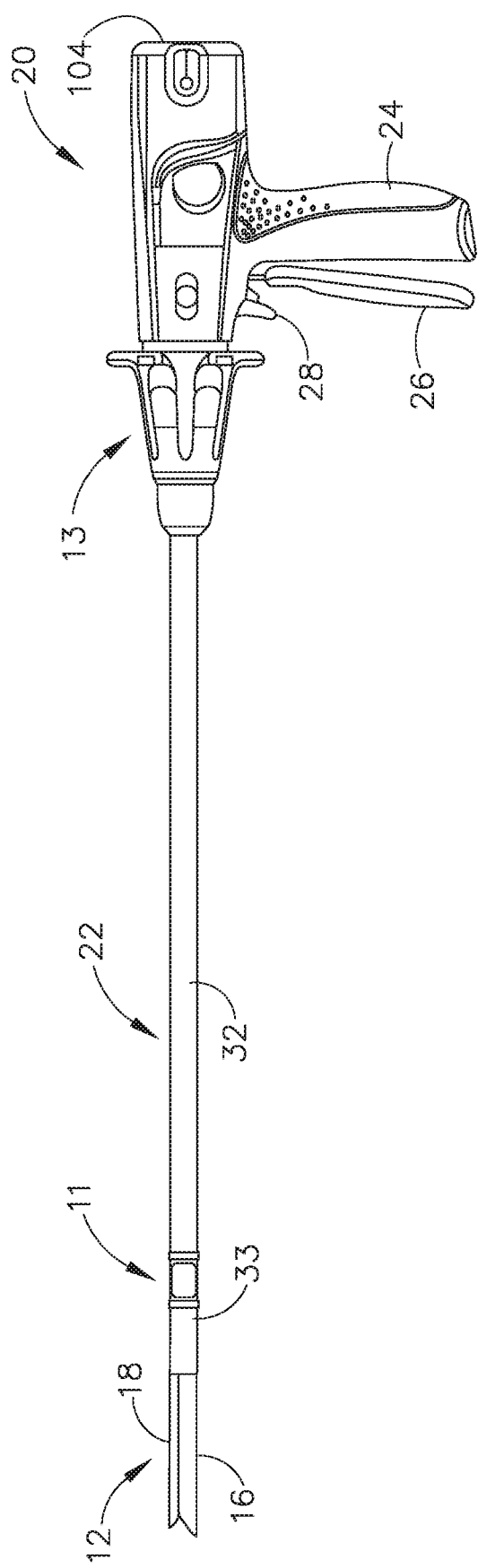
FIG. 2 depicts a side view of the instrument of FIG. 1 with a first exemplary end effector.

Handle portion (20) also includes a firing trigger (28) (shown in FIG. 2). An elongate member (not shown) longitudinally extends through shaft (22) and communicates a longitudinal firing motion from handle portion (20) to a firing beam (14) in response to actuation of firing trigger (28). This distal translation of firing beam (14) causes the stapling and severing of clamped tissue in end effector (12), as will be described in greater detail below.

FIGS. 3-6 depict end effector (12) employing an E-beam form of firing beam (14). As best seen in FIGS. 4A-4B, firing beam (14) includes a transversely oriented upper pin (38), a firing beam cap (44), a transversely oriented middle pin (46), and a distally presented cutting edge (48). Upper pin (38) is positioned and translatable within a longitudinal anvil slot (42) of anvil (18). Firing beam cap (44) slidably engages a lower surface of lower jaw (16) by having firing beam (14) extend through lower jaw slot (45) (shown in FIG. 4B) that is formed through lower jaw (16). Middle pin (46) slidingly engages a top surface of lower jaw (16), cooperating with firing beam cap (44). Firing beam (14) and/or associated lockout features may be constructed and operable in accordance with at least some of the teachings of U.S. Pat. No. 9,717,497, entitled "Lockout Feature for Movable Cutting Member of Surgical Instrument," issued Aug. 1, 2017, the disclosure of which is incorporated by reference herein.

Figure 3:
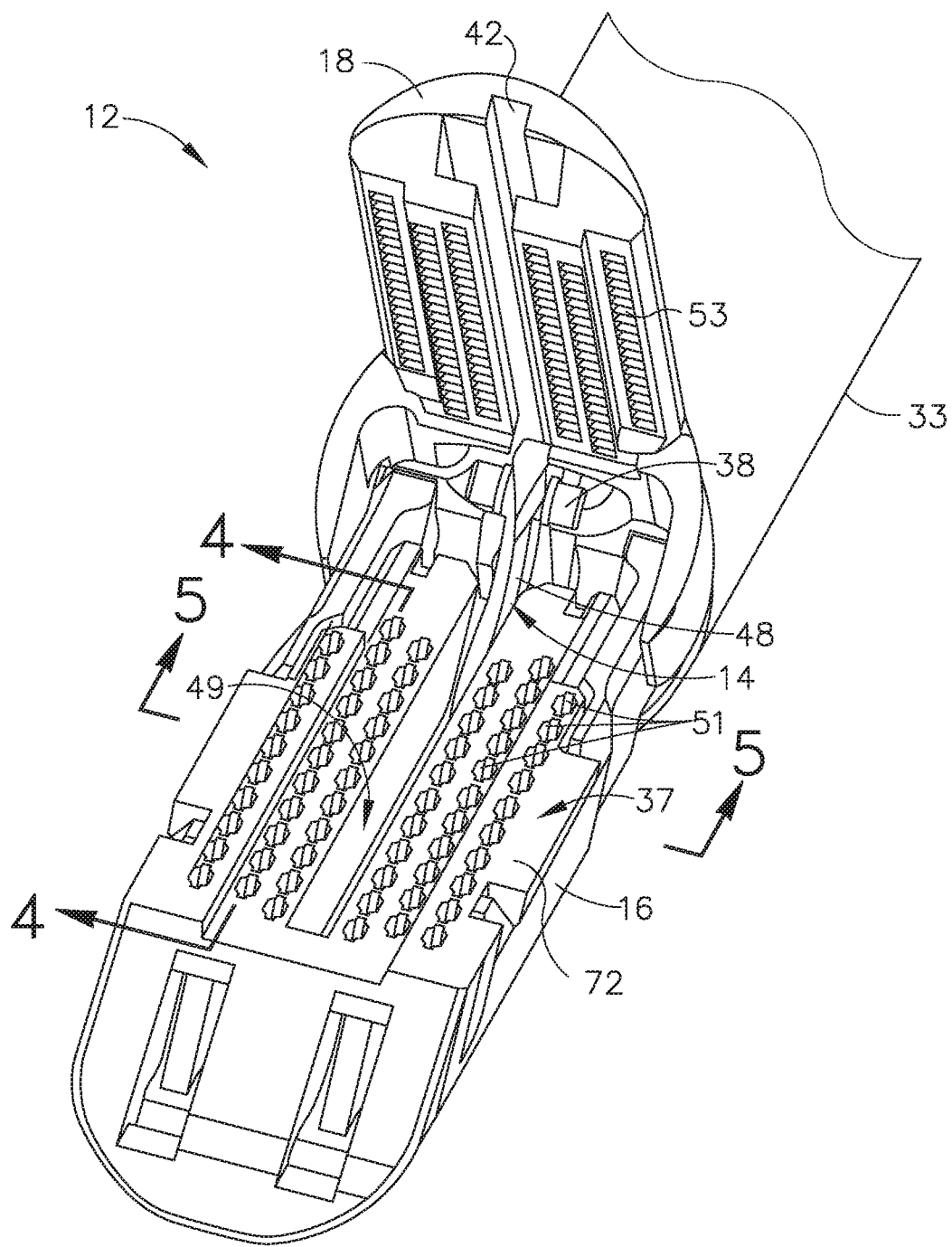
FIG. 3 depicts a perspective view of the end effector of the instrument of FIG. 1 in an open configuration.
Figure 4B:
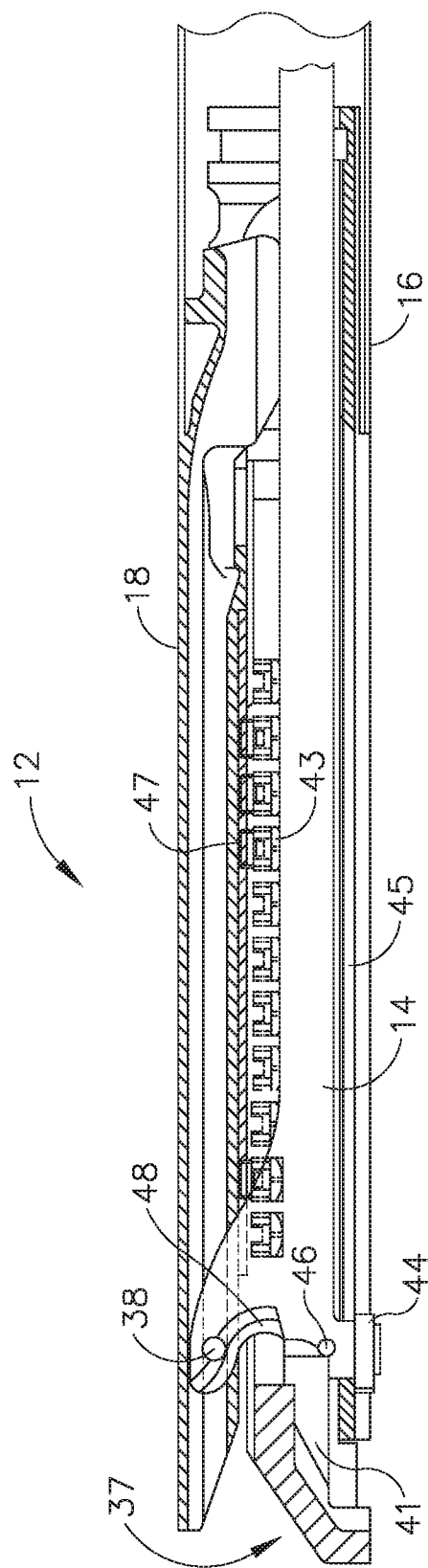
FIG. 4B depicts a side cross-sectional view of the end effector of FIG. 3, taken along line 4-4 of FIG. 3, with the firing beam in a distal position.
Figure 5:
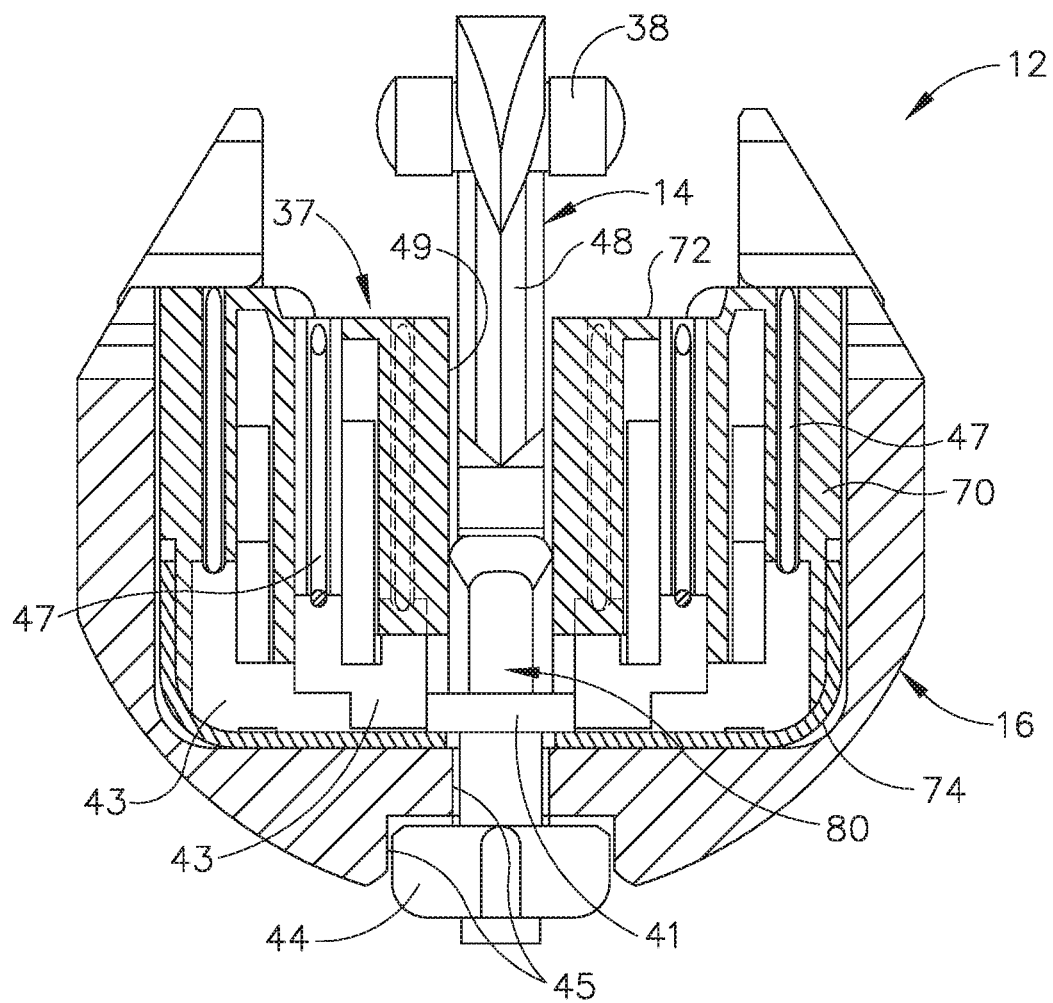
FIG. 5 depicts an end cross-sectional view of the end effector of FIG. 3, taken along line 5-5 of FIG. 3.
Figure 6:
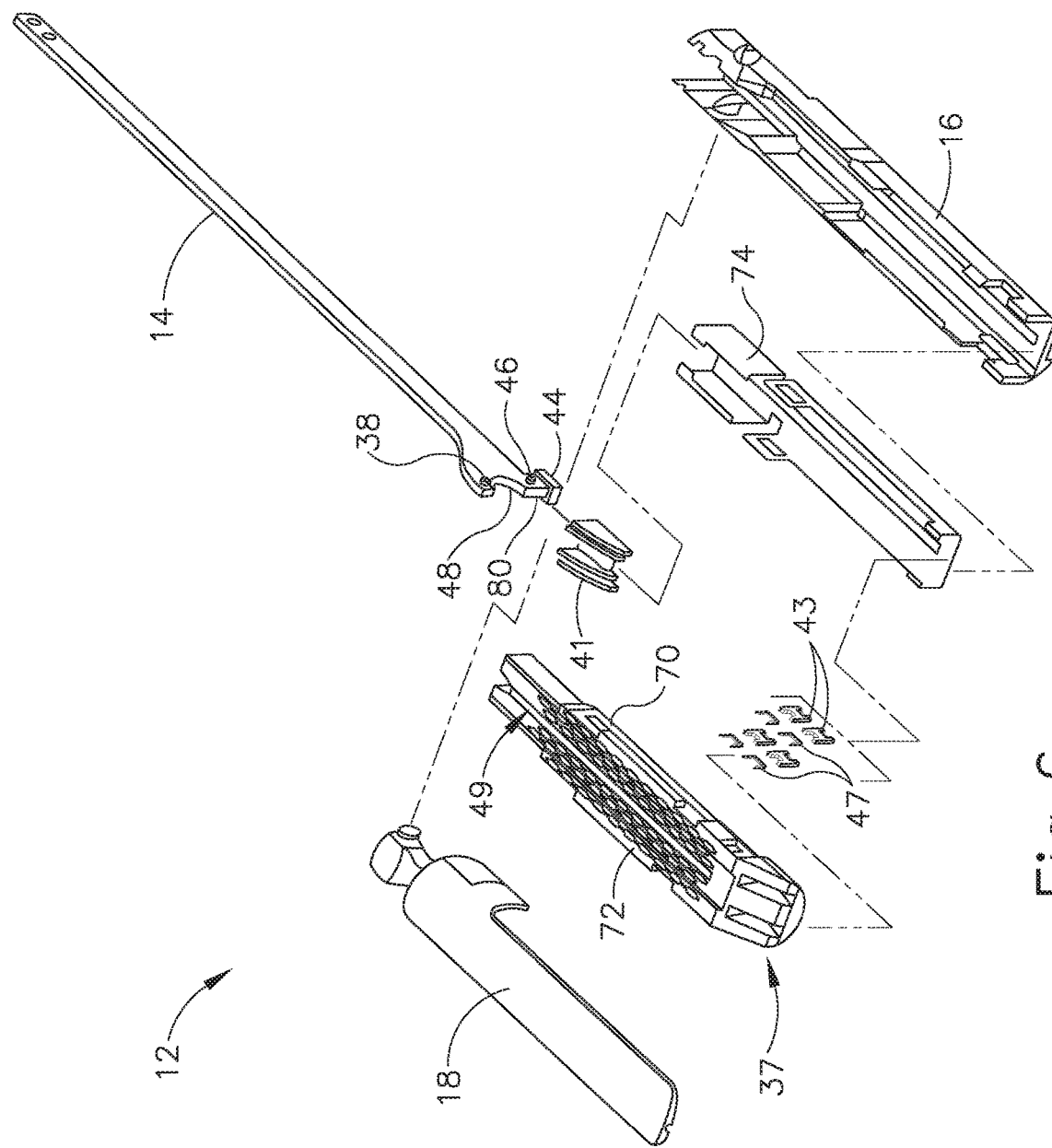
FIG. 6 depicts an exploded perspective view of the end effector of FIG. 3.

FIG. 3 shows firing beam (14) of the present example proximally positioned and anvil (18) pivoted to an open position, allowing an unspent staple cartridge (37) to be removably installed into a channel of lower jaw (16). As best seen in FIGS. 5-6, staple cartridge (37) of this example includes a cartridge body (70), which presents an upper deck (72) and is coupled with a lower cartridge tray (74). As best seen in FIG. 3, a vertical slot (49) is formed through part of staple cartridge (37). As also best seen in FIG. 3, three rows of staple apertures (51) are formed through upper deck (72) on one side of vertical slot (49), with another set of three rows of staple apertures (51) being formed through upper deck (72) on the other side of vertical slot (49). As shown in FIGS. 4A-6, a wedge sled (41) and a plurality of staple drivers (43) are captured between cartridge body (70) and tray (74), with wedge sled (41) being located proximal to staple drivers (43). Wedge sled (41) is movable longitudinally within staple cartridge (37); while staple drivers (43) are movable vertically within staple cartridge (37). Staples (47) are also positioned within cartridge body (70), above corresponding staple drivers (43). Each staple (47) is driven vertically within cartridge body (70) by a staple driver (43) to drive staple (47) out through an associated staple aperture (51). As best seen in FIGS. 4A-4B and 6, wedge sled (41) presents inclined cam surfaces that urge staple drivers (43) upwardly as wedge sled (41) is driven distally through staple cartridge (37). Staple cartridge (37) may be constructed and operable in accordance with at least some of the teachings of U.S. Pat. No. 9,517,065, the disclosure of which is incorporated by reference herein; and/or U.S. Pat. No. 9,808,248, the disclosure of which is incorporated by reference herein.

With end effector (12) closed as depicted in FIGS. 4A-4B by distally advancing closure tube (32) and closure ring (33), firing beam (14) is then advanced in engagement with anvil (18) by having upper pin (38) enter longitudinal anvil slot (42). A pusher block (80) (shown in FIG. 5) is located at the distal end of firing beam (14) and pushes wedge sled (41) as firing beam (14) is advanced distally through staple cartridge (37) when firing trigger (28) is actuated. During such firing, cutting edge (48) of firing beam (14) enters vertical slot (49) of staple cartridge (37), severing tissue clamped between staple cartridge (37) and anvil (18). As shown in FIGS. 4A-4B, middle pin (46) and pusher block (80) together actuate staple cartridge (37) by entering into vertical slot (49) within staple cartridge (37), driving wedge sled (41) into upward camming contact with staple drivers (43), which in turn drive staples (47) out through staple apertures (51) and into forming contact with staple forming pockets (53) (shown in FIG. 3) on the inner surface of anvil (18). FIG. 4B depicts firing beam (14) fully distally translated after completing severing and stapling of tissue. Staple forming pockets (53) are intentionally omitted from the view in FIGS. 4A-4B; but are shown in FIG. 3. Anvil (18) is intentionally omitted from the view in FIG. 5.

Figure 7:
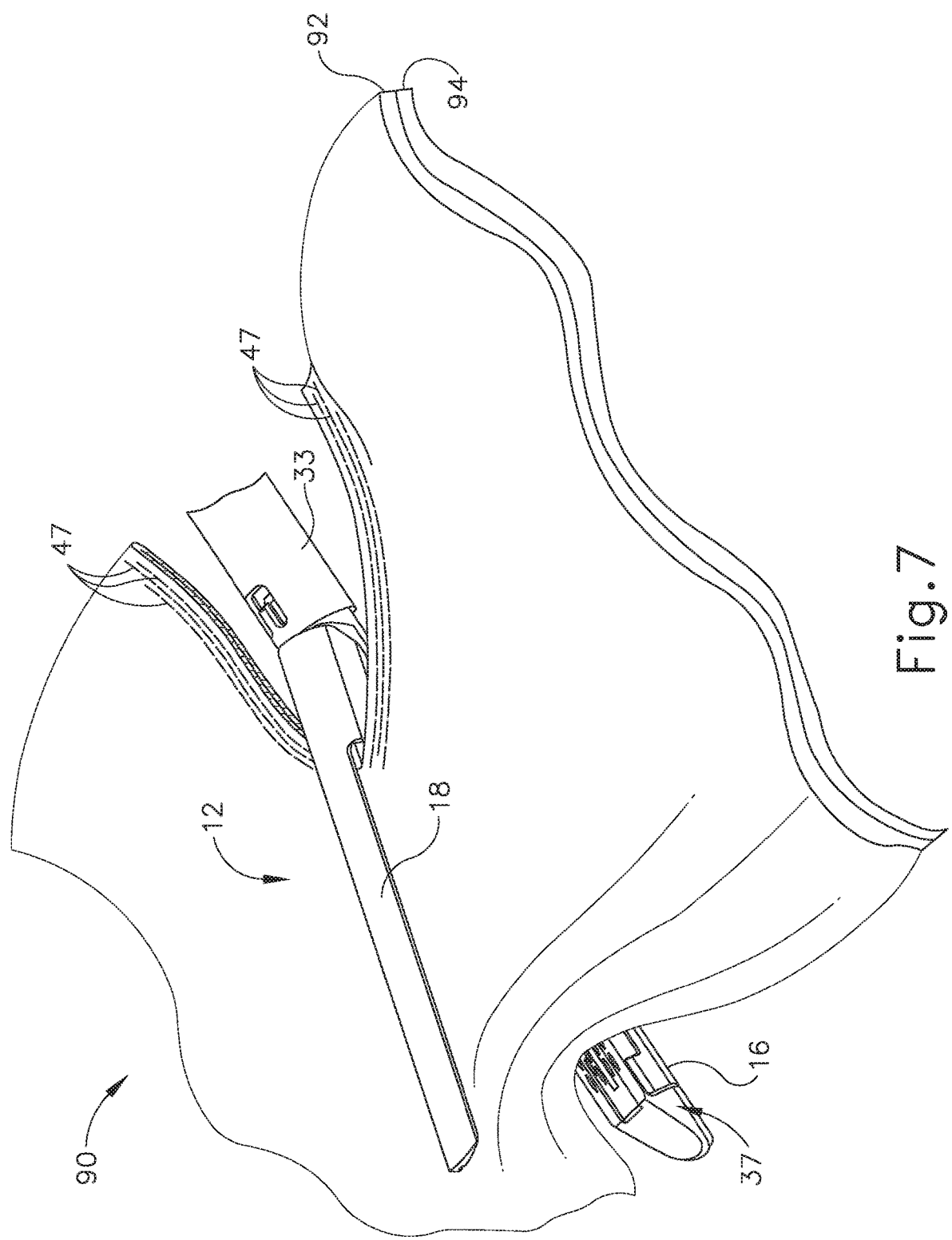
FIG. 7 depicts a perspective view of the end effector of FIG. 3, positioned at tissue and having been actuated once in the tissue.

FIG. 7 shows end effector (12) having been actuated through a single stroke through tissue (90). Cutting edge (48) (obscured in FIG. 7) has cut through tissue (90), while staple drivers (43) have driven three alternating rows of staples (47) through the tissue (90) on each side of the cut line produced by cutting edge (48). End effector (12) is withdrawn from the patient after the first stroke is complete, spent staple cartridge (37) is replaced with a new staple cartridge, and end effector (12) is then again inserted to reach the stapling site for further cutting and stapling. This process may be repeated until the desired number of cuts and staples (47) have been provided.

Some versions of instrument (10) provide motorized control of firing beam (14). Such motorized control may be provided in accordance with at least some of the teachings of U.S. Pat. No. 9,622,746, entitled "Distal Tip Features for End Effector of Surgical Instrument," issued Apr. 18, 2017, the disclosure of which is incorporated by reference herein; and/or U.S. Pat. No. 8,210,411, entitled "Motor-Driven Surgical Instrument," issued Jul. 3, 2012, the disclosure of which is incorporated by reference herein.

In describing the operation of instrument (10), use of the term "pivot" (and similar terms with "pivot" as a base) should not be read as necessarily requiring pivotal movement about a fixed axis. In some versions, anvil (18) pivots about an axis that is defined by a pin (or similar feature) that slides along an elongate slot or channel as anvil (18) moves toward lower jaw (16). In such versions, the pivot axis translates along the path defined by the slot or channel while anvil (18) simultaneously pivots about that axis. In addition, or in the alternative, the pivot axis may slide along the slot/channel first, with anvil (18) then pivoting about the pivot axis after the pivot axis has slid a certain distance along the slot/channel. Such sliding/translating pivotal movement is encompassed within terms such as "pivot," "pivots," "pivotal," "pivotable," "pivoting," and the like.

Instrument (10) may otherwise be configured and operable in accordance with any of the teachings of any of the patent references cited herein. Additional exemplary modifications that may be provided for instrument (10) will be described in greater detail below. The below teachings are not limited to instrument (10) or devices taught in the patents cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. First Exemplary Surgical Instrument Having a Second Exemplary End Effector As end effector (12) is inserted into a surgical site, the user may rotate shaft (22) and end effector (12) of instrument (10) during the procedure. In some instances, lower jaw (16) of end effector (12) is visible rather than anvil (18); while in other instances anvil (18) is visible rather than lower jaw (16). It may be desirable to provide visibility of the surgical site for the user beyond what is possible in instrument (10) of FIG. 1. For instance, in the case of some surgical procedures where fluid carrying vessels are transected and stapled, it may be desirable to have visual confirmation that anvil (18) and lower jaw (16) completely encompass the vessel to be cut, such that the vessel may be fully cut and stapled in one single actuation. It may be desirable to enable the operator to more easily visually confirm proper position of anvil (18) and lower jaw (16) in relation to a vessel to fully clamp the vessel. One potential way of enhancing visualization of the surgical site may include improving visualization of the area adjacent to the distal tip of lower jaw (16) and anvil (18). It may also be desirable to construct end effector (12) such that the distal end of anvil (18) is configured to urge tissue (e.g., a large vessel) proximally into the space between anvil (18) and lower jaw (16) as anvil (18) closes toward lower jaw (16).

Figure 8:
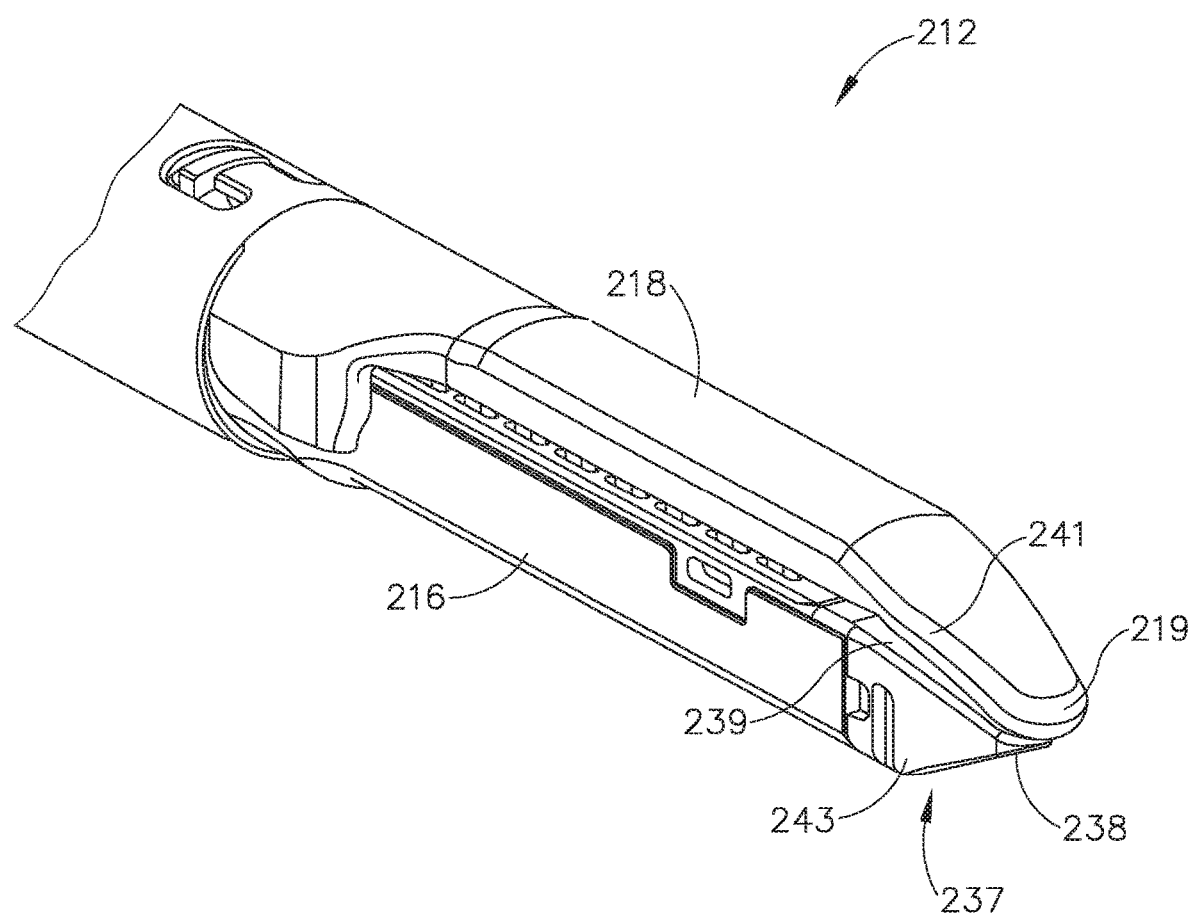
FIG. 8 depicts a perspective view of a second exemplary end effector that includes an angled cartridge and an angled anvil with a tip.

FIG. 8 depicts a second exemplary end effector (212) comprising an anvil (218) and a lower jaw (216). End effector (212) may be used in place of end effector (12) of instrument (10). End effector (212) may be integrally formed with instrument (10) or, in the alternative, may be interchangeable with end effector (12) of instrument (10). Anvil (218) is operable to pivot relative to lower jaw (216). Anvil (218) and lower jaw (216) may clamp tissue (90) similarly to clamping performed by anvil (18) and lower jaw (16)

shown in FIG. 1. End effector (212) further comprises a cartridge (237) operable to be placed in lower jaw (216) similarly to cartridge (37) shown in FIG. 3.

Figure 9:
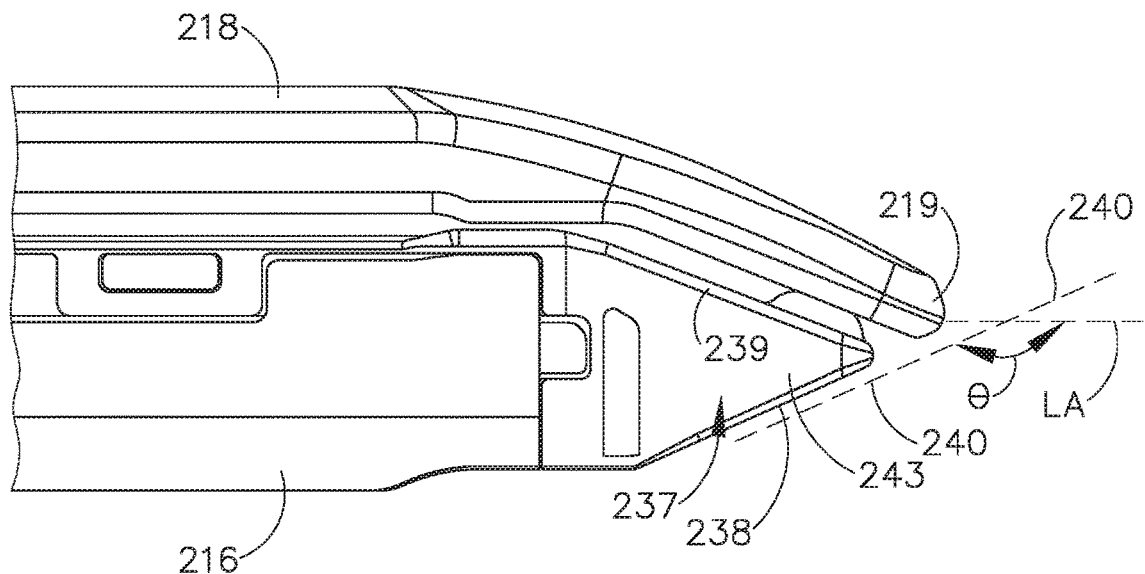
FIG. 9 depicts an enlarged side view of the end effector of FIG. 8.
Figure 10:
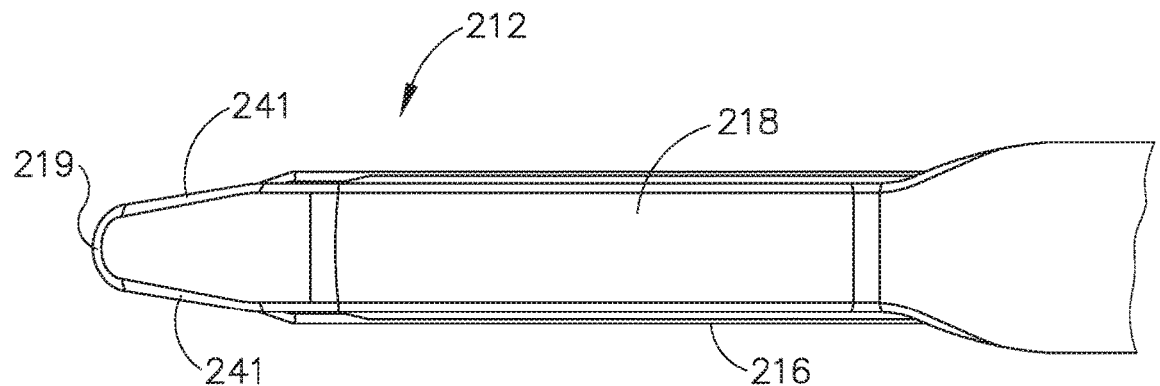
FIG. 10 depicts an enlarged top view of the end effector of FIG. 8.

Anvil (218) as shown in FIGS. 8-10 has an elongated shape where the distal portion of anvil (218) angles toward cartridge (237) such that the distal most tip (219) of anvil (218) extends distally longitudinally further than cartridge (237). Alternatively, distal most tip (219) may extend to a distance longitudinally equal to cartridge (237) or proximal relative to the distal most point on cartridge (237). As seen best in FIG. 10, anvil (218) includes sides (241) that taper laterally as they approach the distal most tip (219) of anvil (218). The angled shape of anvil (218) may provide easier insertion of end effector (212) into a surgical site. For instance, the gentle slope or inverted ski tip shape of anvil (218) may provide an atraumatic tissue deflection surface as anvil (218) contacts or moves through tissue. Such atraumatic tissue deflection may include urging tissue (e.g., a large vessel) proximally into the space between anvil (218) and lower jaw (216) as anvil (218) closes toward lower jaw (216). Once placed into a surgical site, the angled shape of anvil (218) may also provide better maneuverability of end effector (212) and better visibility of the distal end of end effector (212) in relation to anatomical structures at the surgical site.

Cartridge (237) is operable to hold staples like staples (47) shown in FIG. 4A for driving into tissue. As shown in FIG. 9, the distal end of cartridge (237) has a triangular profile defined by an upper tapered surface (239) and a lower tapered surface (238). The distal end of cartridge (237) also comprises a tapered side surface (243) on each side. In the present example, each tapered side surface (243) of cartridge (237) generally aligns with the taper presented by sides (241) of anvil (218). Thus, as shown in FIG. 10, side surfaces (243) of cartridge (237) do not extend outwardly from longitudinal axis (LA) of end effector (212) past sides (241) of anvil (218). Upper tapered surface (239) and lower tapered surface (238) lead to the distal most end of cartridge (237). Lower tapered surface (238) defines a sight line (240) such that once end effector (212) is inserted into a surgical site, the user can see along sight line (240). Sight line (240) extends along the edge of lower tapered surface (238). Sight line (240) intersects longitudinal axis (LA), which extends longitudinally through end effector (212), to form a viewing angle (θ).

The planar shape of lower tapered surface (238) facilitate visualization of the distal most tip (219) of anvil (218). Viewing angle (θ) may establish the relative visibility that a user has of distal most tip (219), such that the user can see in front of distal most tip (219) along any line of sight that passes through the intersection of sight line (240) and longitudinal axis (LA) within viewing angle (θ). As viewing angle (θ) increases, the user would have greater visibility of the area immediately in front of distal most tip (219) from proximal vantage points; whereas as viewing angle (θ) decreases, the user has less visibility of the area in front of distal most tip (219) from proximal vantage points. In some versions, viewing angle (θ) defines an angle greater than 90 degrees. Additionally, in some versions, viewing angle (θ) defines an angle greater than 135 degrees. In the illustrated version, the user generally looks along sight line (240) or along some other line of sight within viewing angle (θ), such that the user has visibility along sight line as well as any area within viewing angle (θ). The underside of distal most tip (219) is further slightly rounded to aid in the visibility of the intersection of longitudinal axis (LA) and sight line (240).

When tissue (90) is clamped between a closed cartridge (237) and anvil (218), the user can look along sight line (240) or elsewhere within viewing angle (θ) to see, for instance, precisely where anvil (218) has clamped tissue (90). Furthermore, the user would be able to determine whether the tissue is completely clamped between anvil (218) and cartridge (237) such that tissue does not spill over the end of end effector (212). The user may be able to also visualize the quality of the clamp between anvil (218) and cartridge (237) against tissue (90). In some instances, end effector (212) may be rotated before, during, or after clamping tissue (90). As a result, the tapered shape of anvil (218) may also provide more accessible viewing of distal most tip (219) or substantially adjacent distal most tip (219). The taper of anvil (218) along with lower tapered surface (238) of cartridge (237) may further promote easy insertion of end effector (212) into tissue in an atraumatic manner. Furthermore, it may be easier to fit end effector (212) through a trocar or other devices operable to introduce end effector (212) into a surgical site due to the tapered end of end effector (212). Lower tapered surface (238) and the tapered shape of anvil (218) may provide a lead-in, guiding the rest of end effector (212) into the trocar. Visibility and maneuverability may thus be enhanced by the tapered design for both sides (241) of anvil (218) and each side (243) of cartridge (237).

In addition to the foregoing, end effector (212) and versions of instrument (10) incorporating end effector (212) may be configured and operable in accordance the teachings of any one or more of the patent references cited herein. Further modifications that may be incorporated into end effector (212) will be described in greater detail below.

In some procedures, it may be necessary to cut along tissue or through tissue where more than one cutting sequence is necessary to complete the procedure—in other words making sequential cuts along a continuous path. In such procedures, this sequential cutting technique can be defined as "marching." With procedures that involve marching, instrument (10) may be placed at the surgical site, actuated to cut and staple, then be removed from the surgical site for installing a new cartridge (37), and then be placed back at the surgical site again for the next cut and staple along the same path in which the previous cutting and stapling cycle occurred. This process is repeated until the cut and staple procedure is complete. As can be seen in FIGS. 4A-4B and FIG. 7, the distal end configuration of end effector (12) provides a gap between the distal end of anvil (18) and the distal end of cartridge (37). This gap may facilitate marching by providing an atraumatic space for tissue to enter the distal end of end effector (12) at the beginning of each marching step.

As noted above, the distal end configuration of end effector (212) is different from the distal end configuration of end effector (12); with the different configuration of end effector (212) providing different potential advantages, such as enhanced visualization, maneuverability, and/or tissue-gathering effects. However, in versions where all the structures of end effector (212) are rigid, the bent configuration of distal most tip (219) of anvil (218) may not lend itself well to marching operations, as distal most tip (219) may impart trauma to tissue that is not gathered into the space between anvil (218) and lower jaw (216) as anvil (218) is closed toward lower jaw (216). Thus, in versions where all the structures of end effector (212) are rigid, end effector (212) may be best suited for cutting and stapling operations (e.g., vessel transection) where all the tissue that is to be cut and stapled is gathered proximal to distal most tip (219).

In view of the foregoing, it may be desirable to provide a variation of end effectors (12, 212) that provides the marching capabilities of end effector (12), the improved visibility, maneuverability, and tissue-gathering effects associated with end effector (212), without providing an increased risk of trauma that might otherwise be associated with fully rigid versions of end effector (212). The following describes several merely illustrative examples of such variations of end effectors (12, 212). In the following examples, an anvil has a distal tip that is resiliently biased to assume a bent or angled configuration like distal tip (219); yet the resiliently biased distal tip is deflectable away from the lower jaw in response to a sufficient load on the distal tip. Providing a deformable tip can provide an additional level of maneuverability benefits in terms of navigating through tissue to a surgical site. In this manner, the deformable tip may deflect or deform to promote smooth and atraumatic movement of the end effector through tissue, particularly during marching operations.

Figure 11:
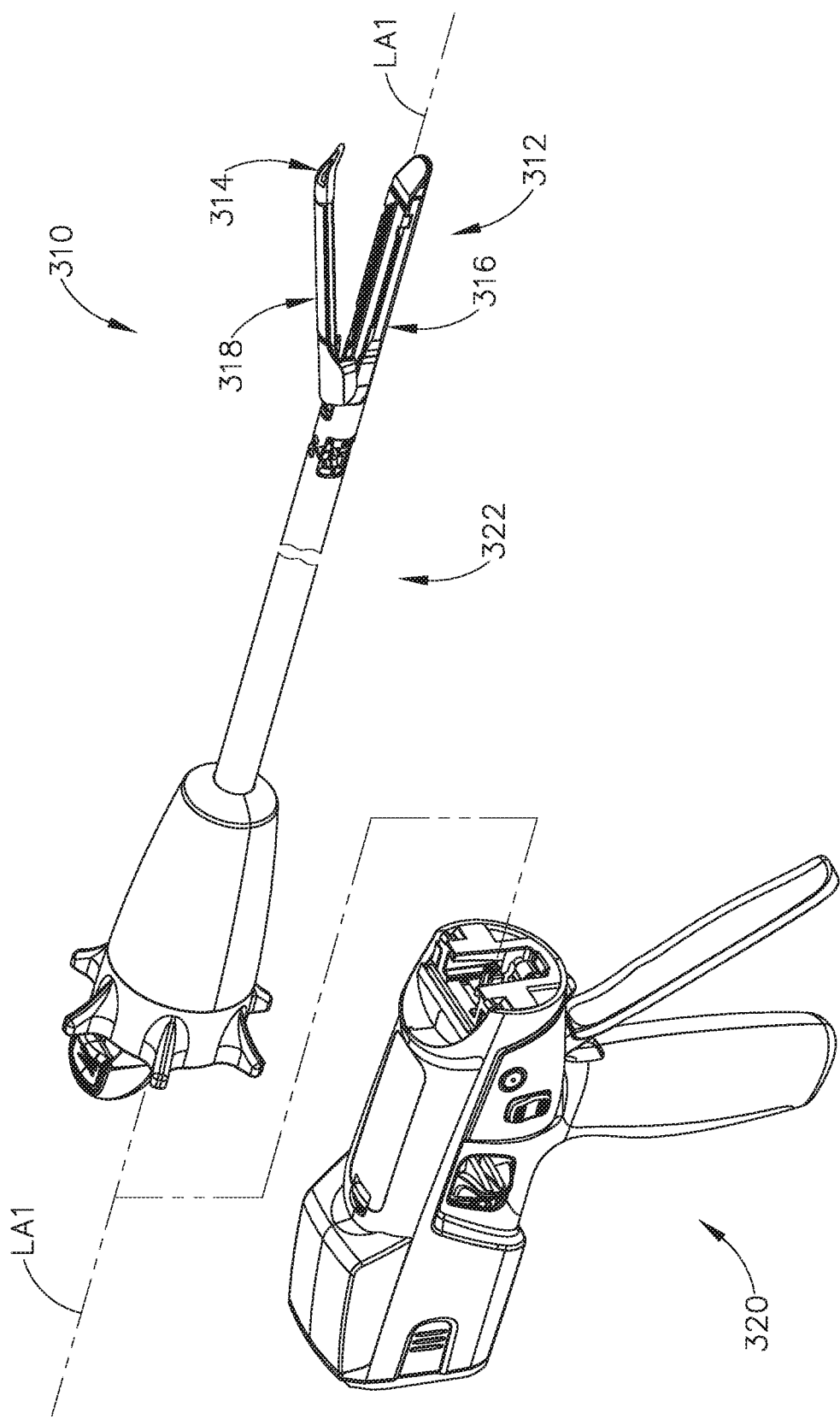
FIG. 11 depicts a perspective view of a second exemplary surgical stapling instrument with a third exemplary end effector with a first exemplary placement tip, where the upper and lower jaws are in an open configuration.

III. Second Exemplary Surgical Instrument Having Various End Effectors and Placement Tips FIG. 11 shows a second exemplary surgical instrument (310) configured as a surgical stapler. Instrument (310) comprises a handle portion (320) and a shaft (322). Shaft (322) defines a longitudinal axis (LA1) that extends from handle portion (320). Instrument (310) has a modular configuration such that shaft (322) is selectively removable from, and attachable to, handle portion (320). Instrument (310) is configured similarly to instrument (10), such that the operability and use of instrument (310) is the same as described above for instrument (10) with the added feature of instrument (310) being a modular configuration. With its modular configuration, instrument (310) provides a way to change the desired end effector. Features operable for providing the modular configuration of instrument (310) may be configured in accordance with at least some of the teachings of U.S. Pub. No. 2017/0086823, entitled "Surgical Stapling Instrument with Shaft Release, Powered Firing, and Powered Articulation," published Mar. 30, 2017, issued as U.S. Pat. No. 10,182,813 on Jan. 22, 2019, the disclosure of which is incorporated by reference herein; and/or U.S. Pat. No. 9,913,642, entitled "Surgical Instrument Comprising a Sensor System," issued Mar. 13, 2018, the disclosure of which is incorporated by reference herein. In some other versions, shaft (322) is not detachable from handle portion (320).

As will be discussed in greater detail below, exemplary end effectors (312, 412, 512) are provided on shaft (322) that is detachable from handle portion (320). End effectors (312, 412, 512) are operable to compress, staple, and cut tissue. End effectors (312, 412, 512) may be used in place of end effector (12) shown in FIG. 1. In some versions, end effectors (312, 412, 512) may be integrally formed with shaft (322) or, alternatively, may be separately formed and then combined. In some versions, end effectors (312, 412, 512) may be provided for use in robotic systems. In such robotic systems, modular shaft (322) having any of the following end effectors (312, 412, 512) may be attachable to a portion of the robotic system for use such that handle portion (320) is replaced by components of the robotic system, including a body. Other ways to incorporate an end effector (312, 412, 512) having any of the following placement tips (314, 414, 514) into a user operated or robotic operated instrument will be apparent to those of ordinary skill in the art.

As will be described in greater detail below, placement tips (314, 414, 514) are configured to be coupled with an upper jaw (such as anvil 318, 418, 518) or a lower jaw (316, 416, 516). Placement tips (314, 414, 514) may be positioned on the same jaw as staple cartridge (37) or on the same jaw as anvil (318, 418, 518). Placement tips (314, 414, 514) are operable to elastically deform from a first angled position to a second angled position. The second angled position for placement tips (314, 414, 514) may be substantially straight in some versions, but may be angled to a degree (e.g., slightly above or slightly below the longitudinal axis (LA1, LA2, LA3)) in other versions. The second angled position for placement tips (314, 414, 514) may be defined by the characteristics (e.g., thickness, density, etc.) of the tissue that is being captured between anvils (318, 418, 518) and lower jaws (316, 416, 516) and/or central voids (332, 436, 536) that are located at least partially within placement tips (314, 414, 514) as will be discussed in greater detail below. Central voids (332, 436, 536) allow placement tips (314, 414, 514) to be formed from stiffer, more rigid, materials. Central voids (332, 436, 536) enable placement tips (314, 414, 514) to deflect in part due to their spatial geometries. While shown as central voids (332, 436, 536), voids may not necessarily be in the geometric center and may be offset a distance from the geometric center.

The exemplary placement tips (314, 414, 514) described below may be used with any surgical instrument (10, 310) described above and below and in any of the various procedures described in the various patent references cited herein. As will be described in greater detailed below, placement tips (314, 414, 514) may be used singularly or in combination with other placement tips, such as placement tips (314, 414, 514). To this end, like numbers below indicate like features described above. Except as otherwise described below, instrument (310) described below may be constructed and operable like instrument (10) described above. Certain details of instrument (310) will therefore be omitted from the following description, it being understood that such details are already provided above in the description of instrument (10). Other suitable ways in which various surgical instruments may be used will be apparent to those of ordinary skill in the art in view of the teachings herein.

Figure 12:
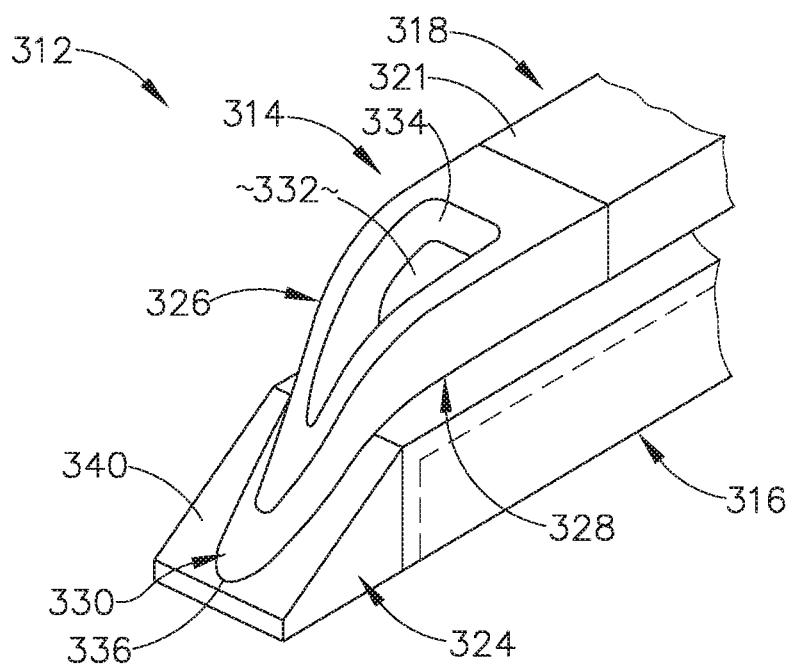
FIG. 12 depicts an enlarged schematic perspective view of the end effector of FIG. 11 with the placement tip and the lower jaw in a closed configuration.
Figure 13:
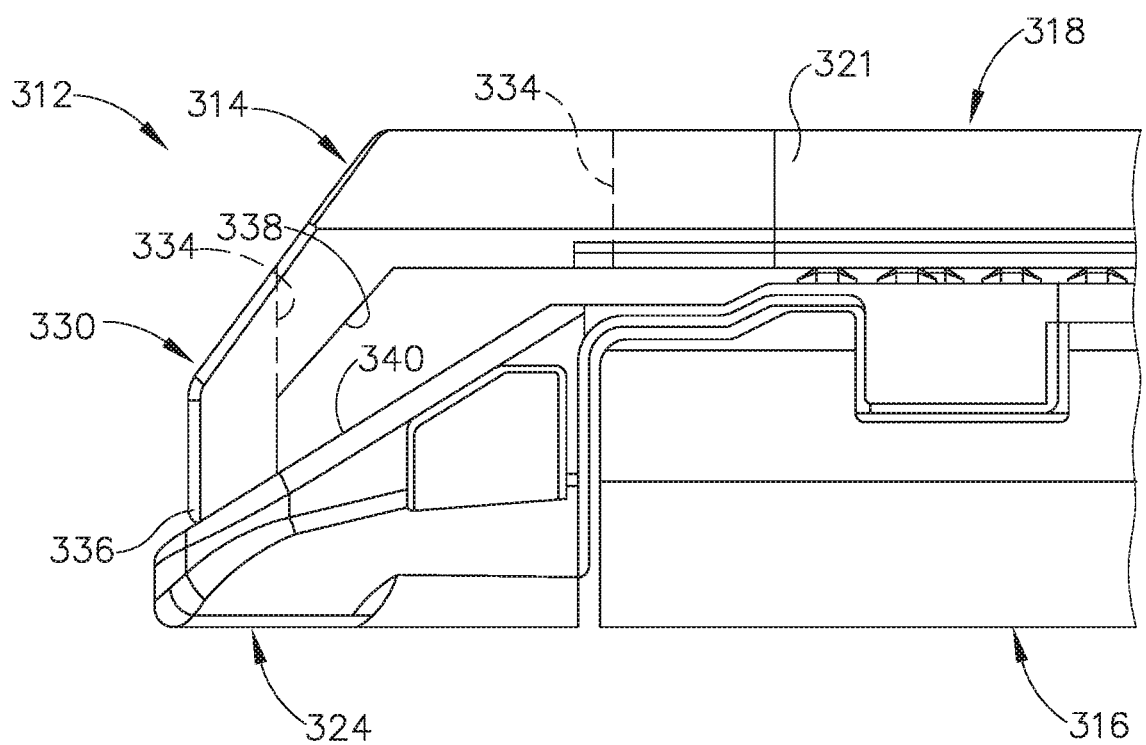
FIG. 13 depicts a schematic side view of the end effector of FIG. 12 in the closed configuration.
Figure 14:
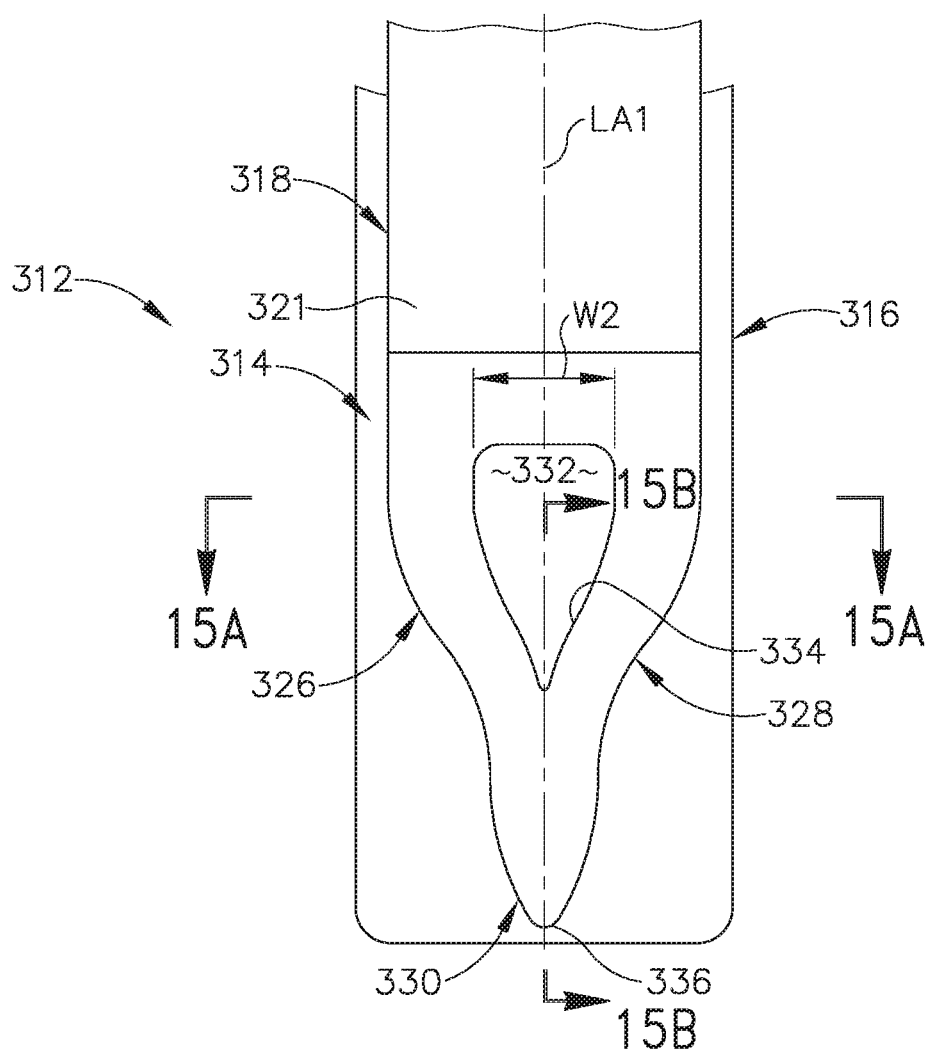
FIG. 14 depicts a schematic top view of the placement tip and anvil of FIG. 12.

A. Second Exemplary Surgical Instrument Having a Third Exemplary End Effector and a First Example of a Placement Tip FIGS. 11-15B show a second exemplary surgical instrument (310) that comprises a third exemplary end effector (312) and a first exemplary placement tip (314). FIGS. 12-14 show enlarged views of a distal end of end effector (312) shown in FIG. 11. As shown, end effector (312) includes an upper jaw (shown as including an anvil (318)), and a lower jaw (316). While anvil (318) is included in an upper jaw, and cartridge (324) is received in lower jaw (316), this relationship may be reversed. Lower jaw (316) is shown schematically in FIG. 12, and in greater detail in FIG. 13. Staple cartridge (324) is removably coupled with lower jaw (316). As described above with respect to staple cartridge (37), staple cartridge (324) is configured to hold one or more staples.

At least one of anvil (318) or lower jaw (316) is movable relative to other of anvil (318) or lower jaw (316) between an open configuration and a closed configuration. As shown, anvil (318) pivotably rotates toward lower jaw (16) in the same manner as anvil (18) as described above with respect to instrument (10). In this manner, end effector (312) is similar to end effector (12), however, placement tip (314) is elastically deformable. Placement tip (314) obtains a first angled position, shown in FIGS. 12 and 13, when end effector (312) is not clamping tissue. In this first angled position, end effector (312) may be in an open configuration as shown in FIG. 11, or a closed configuration as shown in FIGS. 12 and 13. Specifically regarding the closed configuration, FIG. 13 shows distal tip (336) is in contact with angled surface (340). In instances when end effector (312) is in this angled configuration, end effector (312) may be considered in a non-loaded state or non-loaded position. Conversely, in a second angled position when end effector (312) is clamping tissue, end effector (312) may be considered in a loaded state or a loaded position. In the second angled position, at least a portion of placement tip (314) deflects upwardly.

Figure 18:
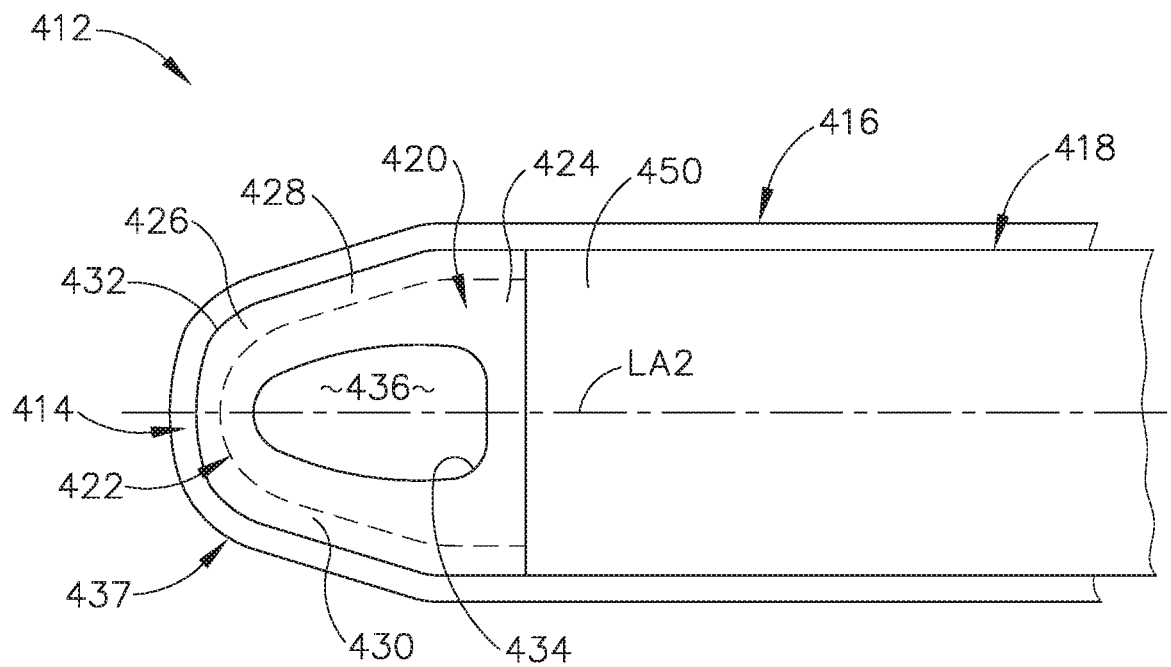
FIG. 18 depicts a top view of a fourth exemplary end effector that includes a lower jaw as well as the anvil and the placement tip of FIG. 16.

Placement tip (414) is located adjacent at least one of distal end (450) of the anvil (418) or a distal end of lower jaw (416). As shown in FIGS. 18-20B, placement tip (414) is coupled with a distal end (450) of anvil (418). As shown in FIGS. 20A-20B, lower jaw (416) is thicker (i.e. vertically taller) than anvil (418) or placement tip (414). Additionally, as shown in the top view of FIG. 18, lower jaw (416) is longer and wider than anvil (418) and placement tip (414). As shown in FIG. 18, placement tip (414) is symmetric about a longitudinal axis (LA2). However, placement tip (414) may be non-symmetric, if desired.

Figures 15A, 15B:
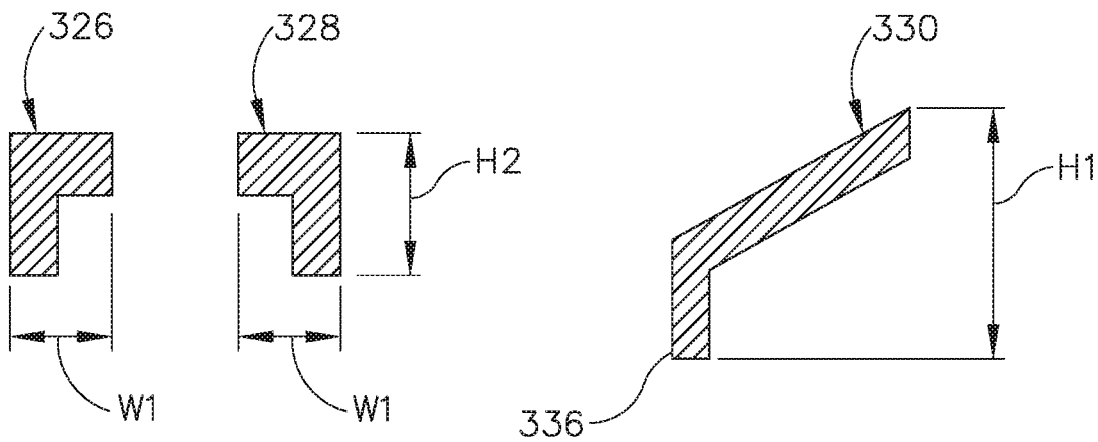
FIG. 15A depicts a transverse cross-sectional view of first and second legs of the placement tip of FIG. 14, taken along line 15A-15A of FIG. 14.
FIG. 15B depicts a longitudinal cross-sectional view of a distal portion of the placement tip of FIG. 14, taken along line 15B-15B of FIG. 14.

Placement tip (314) includes first and second legs (326, 328) and a distal portion (330). As shown, first and second legs (326, 328) extend distally from anvil (318). First and second legs (326, 328) are separated by central void (332), which is shown as extending completely through placement tip (314). With reference to FIG. 15A, first and second legs (326, 328) have a generally L-shaped cross-section. Additionally, first and second legs (326, 328) each have a first width (W1) shown in FIG. 15A that is less than a second width (W2) of a central void (332) shown in FIG. 14. Central void (332) is defined by an inner wall (334) extending through placement tip (314). While FIG. 14 shows central void (332) being generally pentagon shaped when viewed from above, central void (332) may have a variety of different shapes and/or sizes depending on the desired degree of upward flexibility according to the specific orientation shown. Additionally, while inner wall (334) forming central void (332) is shown as extending generally perpendicular to longitudinal axis (LA1) of placement tip (314), inner wall (334) may alternatively be angled, if desired.

Distal portion (330) of placement tip (314) connects first and second legs (326, 328). As shown in FIGS. 15A-15B, distal portion (330) has a first cross-sectional height (H1) that is greater than second cross-sectional height (H2) of first and second legs (326, 328). Since H1 is greater than H2, placement tip (314) is elastically deformable. More specifically, since distal portion (330) has a first cross-sectional height (H1) that is greater than second cross-sectional height (H2) of first and second legs (326, 328), the first and second legs (326, 328) deflect before distal portion (330) deflects, allowing distal portion (330) to remain generally rigid. Additionally, central void (332) allows first and second legs (326, 328) of placement tip (314) to deflect upwardly when in contact with tissue. This spatial geometry of placement tip (314) allows placement tip (314) to be formed from a rigid material, while still retaining the desired degree of flexibility.

Additionally, distal portion (330) of placement tip (312) terminates at distal most point (336), which may be blunt or sharp. When distal tip (336) is rigid, such as when a portion of or the entire placement tip (314) is formed from a rigid material, distal tip (336) allows for jabbing at small areas of tissue and subsequent dilatation of the area of tissue as placement tip (314) is advanced distally. Additionally, in the closed configuration, since distal portion (330) maybe in contact with lower jaw (316), distal tip (336) may be sharp because distal tip (336) is shielded from damaging tissue by lower jaw (316). In other versions, placement tip (312) is deformable. Such deformability may be elastic or malleable.

B. Second Exemplary Surgical Instrument Having a Fourth Exemplary End Effector and a Second Example of a Placement Tip FIGS. 16-20B show a fourth exemplary end effector (412) and a second exemplary placement tip (414). As shown, end effector (412) comprises upper and lower opposing jaws, a staple cartridge (437) similar to staple cartridge (37, 324), and placement tip (414). While the upper jaw includes anvil (418) and lower jaw (416) accepts staple cartridge (437), this relationship may be reversed. Placement tip (414) may be permanently coupled with or removably coupled with an anvil (418). Lower jaw (416) is similar to lower jaw (16). Staple cartridge (437) is removably coupled with lower jaw (416) in a similar manner to staple cartridge (37) and lower jaw (16) and is configured to hold one or more staples.

At least one of anvil (418) or lower jaw (416) is movable relative to other of anvil (418) or lower jaw (416) between an open configuration and a closed configuration. As shown, anvil (418) pivotably rotates toward lower jaw (416) in the same manner as anvil (18) as described above with respect to instrument (10). In this manner, end effector (412) is like end effector (12). However, placement tip (414) is elastically deformable. Placement tip (414) assumes a first angled position, shown in FIG. 20A, when end effector (412) is not clamping tissue. In this first angled position, end effector (412) may be in an open configuration like what is shown in FIG. 11; or a closed configuration as shown in FIG. 20A where placement tip (414) is in contact with staple cartridge (437) of lower jaw (416). In instances when end effector (412) is in the first angled configuration, end effector (412) may be considered in a non-loaded state or non-loaded position. Conversely, while not shown, in a second angled position when end effector (412) is clamping tissue, end effector (412) may be considered in a loaded state or a loaded position. In the second angled position, at least a portion of placement tip (414) deflects upwardly.

Placement tip (414) is located adjacent at least one of distal end (450) of the anvil (418) or a distal end of lower jaw (416). As shown in FIGS. 18-20B, placement tip (414) is coupled with a distal end (421) of anvil (418). As shown in FIGS. 20A-20B, lower jaw (416) is thicker (i.e. vertically taller) than anvil (418) or placement tip (414). Additionally, as shown in the top view of FIG. 18, lower jaw (416) is longer and wider than anvil (418) and placement tip (414). As shown in FIG. 18, placement tip (414) is symmetric about a longitudinal axis (LA2). However, placement tip (414) may be non-symmetric, if desired.

FIGS. 16-20B show placement tip (414) as including a body portion (420) and a malleable member (422). Body portion (420) includes proximal and distal portions (424, 426) separated by first and second legs (428, 430). Body portion (420) is formed between an outer perimeter (432) and an inner perimeter (434) of placement tip (414). Inner perimeter (434) is defined by a central void (436) extending through placement tip (412). At least a portion of distal portion (426) of body portion (420) is bent towards the opposing jaw, shown as lower jaw (416). At least body portion (420) of placement tip (314) may be integrally formed together as unitary piece.

Figure 19:
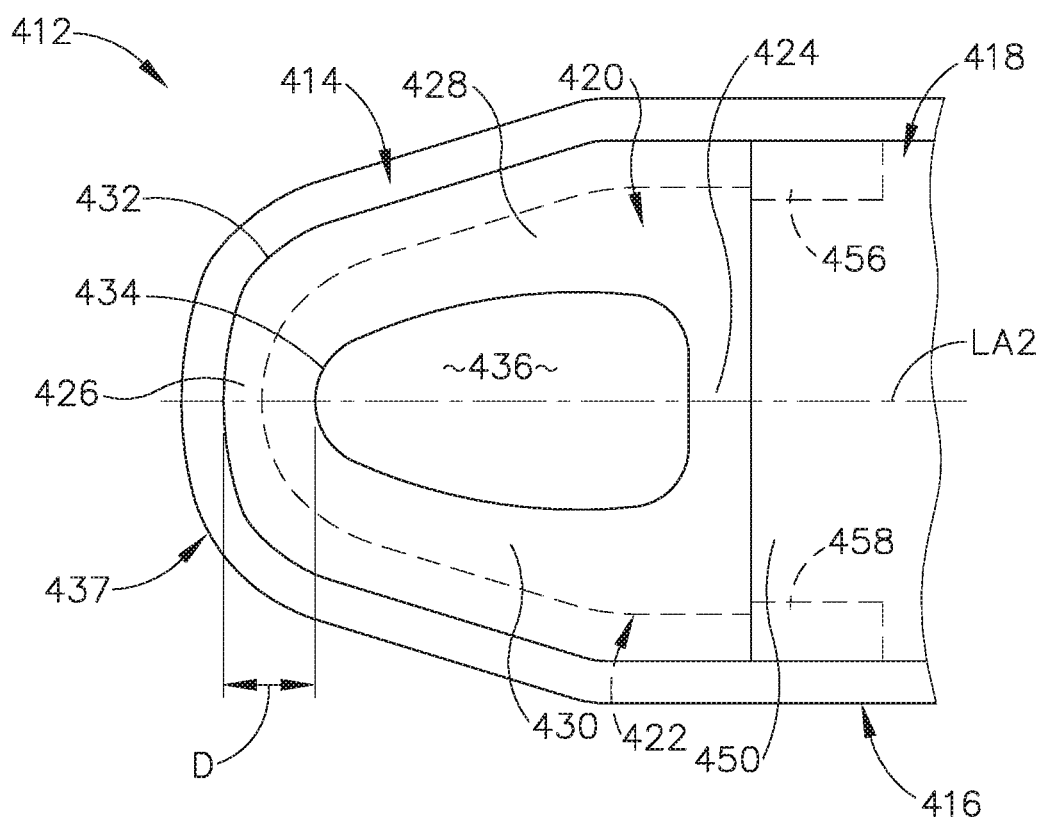
FIG. 19 depicts an enlarged top view of the placement tip of FIG. 18.
Figure 20A:
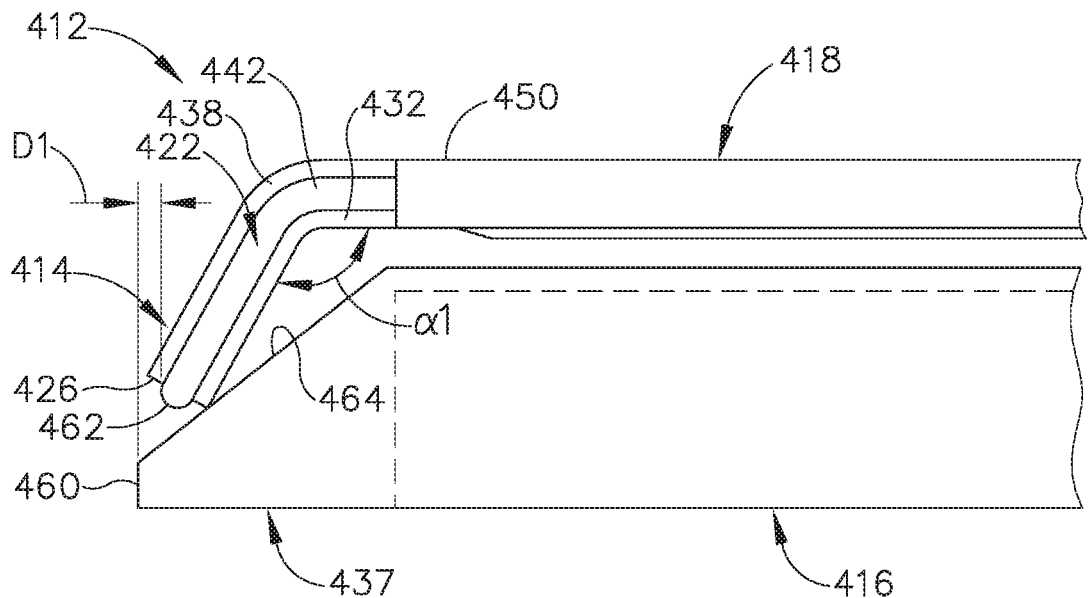
FIG. 20A depicts a side view of the placement tip of FIG. 18 in a first bent configuration.
Figure 20B:
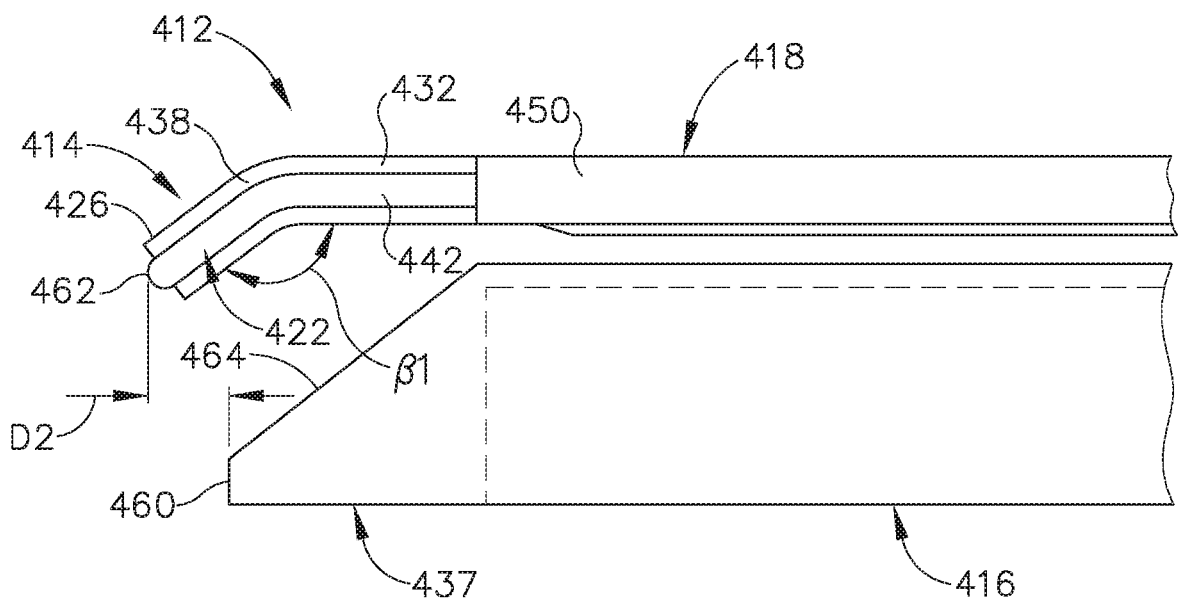
FIG. 20B depicts a side view of the placement tip of FIG. 18 in a second bent configuration.
Figure 21:
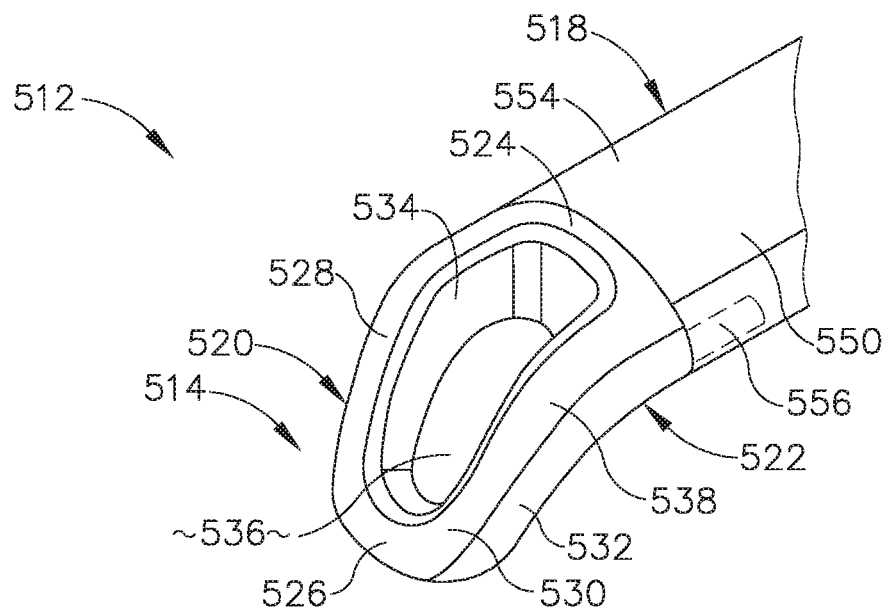
FIG. 21 depicts a perspective view of a third exemplary placement tip with a malleable member embedded within the placement tip.

Additionally, as shown in FIGS. 16-19, and more clearly in the top views of FIGS. 18-19, each of body portion (420) and central void (436) have a generally oval shape when viewed from the top. In the example shown, central void (436) is egg-shaped and is wider adjacent proximal portion (424) than adjacent distal portion (426). Additionally, central void (436) formed by inner perimeter (434) forms a full oval (i.e. a 360-degree oval). Body portion (420) is oval shaped and forms about half oval (i.e. a 180-degree oval). As shown in FIG. 19, the distance (D) between outer perimeter (432) and inner perimeter (434) is generally uniform. Placement tip (414) includes a bend (438) disposed along longitudinal axis (LA2) producing a bent oval placement tip shape at least in the first angled state shown in FIGS. 16-17 and 20A-20B. As shown in FIGS. 20A-20B, bend (438) directs placement tip (414) toward staple cartridge (437) of lower jaw (416).

Figure 16:
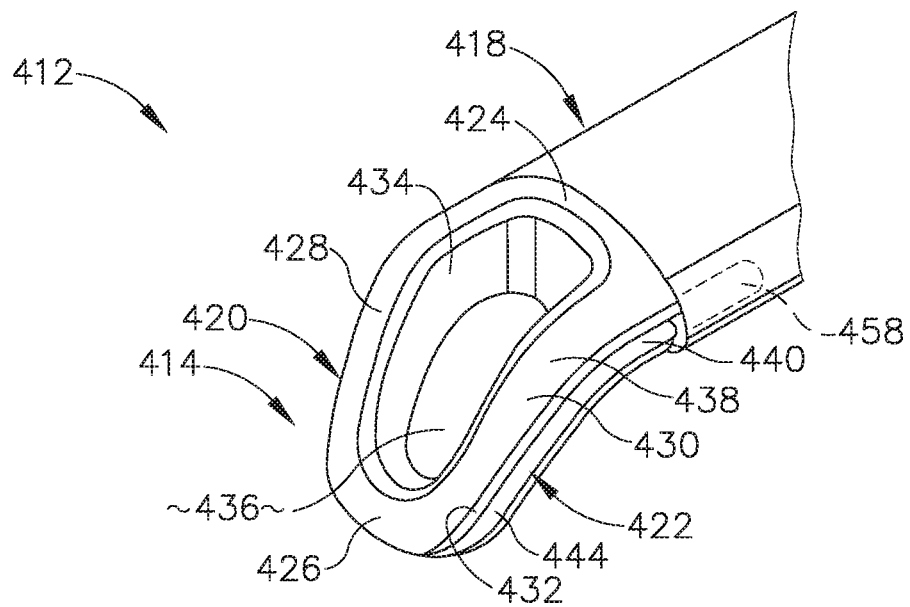
FIG. 16 depicts a perspective view of an anvil and a second exemplary placement tip with a malleable member.
Figure 17:
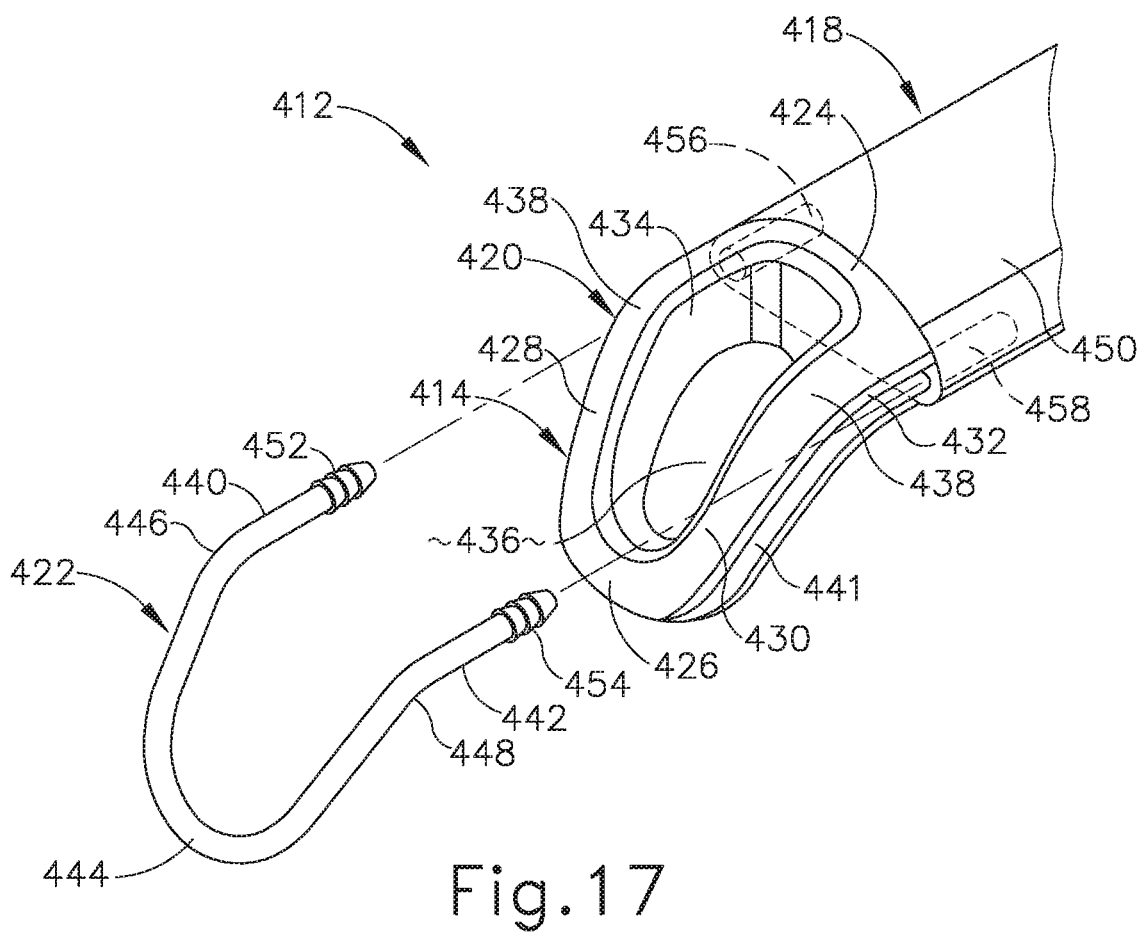
FIG. 17 depicts an exploded perspective view of the anvil and the placement tip of FIG. 16, but with the malleable member separated from the placement tip.

As shown in FIGS. 16 and 17, malleable member (422) fits in a generally U-shaped channel (441) disposed in outer perimeter (432) of body portion (420). Channel (441) may take the form of a variety of shapes and sizes, and may even be entirely omitted. As shown in FIG. 17, malleable member (422) includes first and second legs (440, 442) and generally U-shaped portion (444) configured to contact outer perimeter (432) of body portion (420). Malleable member (422) also includes first and second bent portions (446, 448). Malleable member (422) allows for ad hoc customization of the bend angle.

As previously described, malleable member (422) may be removably coupled with at least one of placement tip (414) or the jaw that includes placement tip (414), which is shown as such as anvil (418). Alternatively, while not shown, if placement tip (414) is desired to be coupled with lower jaw (416), malleable member (422) may be removably coupled with at least one of placement tip (414) or lower jaw (416). Distal end (450) of anvil (418) includes at least one coupling feature that is configured to mate with at least one coupling feature of malleable member (422). As shown, the coupling features of malleable member (422) include first and second barbed fittings (452, 454). The coupling features disposed at distal end (450) of anvil (418) are configured to be in locking engagement with first and second corresponding receptacles (456, 458) configured to securably couple with first and second barbed fittings (452, 454). For this reason, the interior of first and second receptacles (456, 458) may include a non-smooth surface.

As shown in FIGS. 20A-20B, malleable member (422) is configured to increase the rigidity of placement tip (414) and allow an operator to customize the shape of placement tip (414) by producing different angles of placement tip (414). For example, FIG. 20A may refer to a pre-customized standard angle alpha (α1), while FIG. 20B may refer to a post-customized angle beta (β1). As shown, angle alpha (α1) is less than angle beta (β1). As shown in the pre-customized configuration of FIG. 20A, a distal end (460) of cartridge (437) extends a first distance (D1) beyond distal portion (426) of placement tip (414). Angled surface (464) of cartridge (437) is in contact with a distal portion (426) of placement tip (414). However, in the post-customized configuration of FIG. 20B, distal portion (426) of placement tip (414) extends a second distance (D2) beyond distal end (460) of cartridge (437). Distal tip (462) of malleable member (422) may extend beyond distal portion (426) of body portion (420). Additionally, it is envisioned that the operator may use different malleable members (422) having various different stiffnesses to obtain the desired amount of rigidity of placement tip (414).

C. Second Exemplary Surgical Instrument Having a Fifth Exemplary End Effector and a Third Example of a Placement Tip FIGS. 21-23B show a fifth exemplary end effector (512) that comprises an upper jaw, a lower jaw (516), a staple cartridge (537) (like staple cartridge (37)), and a third exemplary placement tip (514). As shown, the upper jaw includes anvil (518). Lower jaw (516) is like lower jaw (16). Staple cartridge (537) is removably coupled with lower jaw (516) in a similar manner and function as lower jaw (16) and staple cartridge (37) described above. Staple cartridge (537) is configured to hold one or more staples. At least one of anvil (518) or lower jaw (516) is movable relative to other of anvil (518) or lower jaw (516) between an open configuration (shown in FIG. 11 with respect to end effector (312)) and a closed configuration shown in FIGS. 23A-23B. Anvil (518) pivotably rotates toward lower jaw (516) in a similar manner as anvil (18) as described above with respect to instrument (10). End effector (512) is thus like effector (12), but with anvil (518) comprising placement tip (514) that is elastically deformable. While not shown, placement tip (514) may be located adjacent one or both of a distal end (550) of the anvil (518) or a distal end of lower jaw (516).

Figure 22:
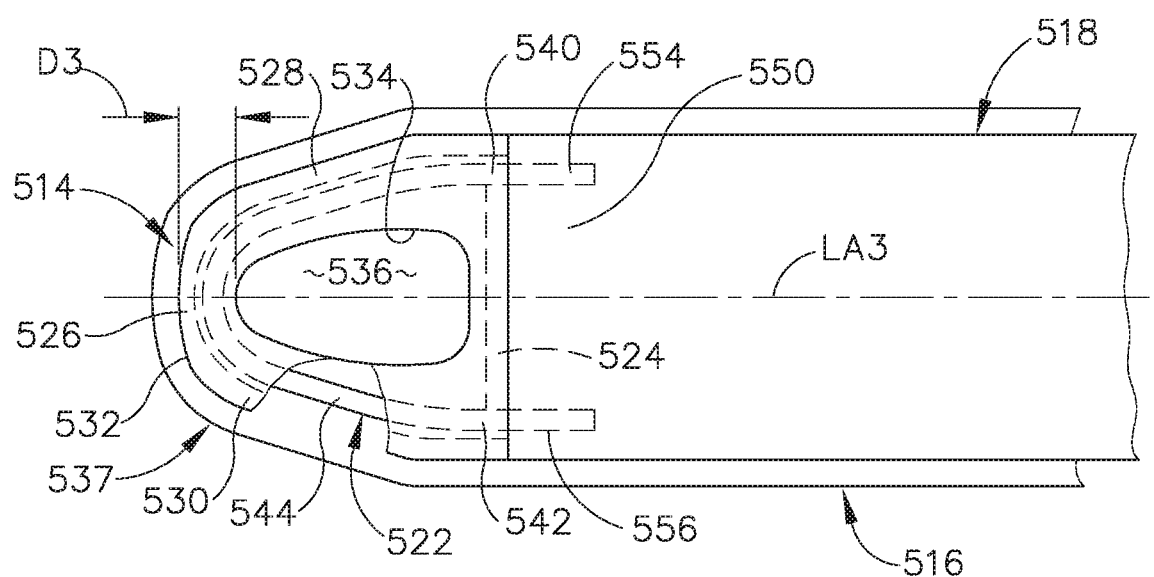
FIG. 22 depicts a top view a fifth exemplary end effector that includes a lower jaw as well as the anvil and the placement tip of FIG. 21.

As shown in 21-23B, placement tip (514) includes a body portion (520) and a malleable member (522). Placement tip (514) is like placement tip (414) described above, but malleable member (522) is permanently coupled with body portion (520). Body portion (520) includes proximal and distal portions (524, 526) separated by first and second legs (528, 530). Body portion (520) is formed between an outer perimeter (532) and an inner perimeter (534) of placement tip (514). Inner perimeter (534) is defined by a central void (536) extending through placement tip (514). At least a portion of distal portion (526) of body portion (520) is bent toward the opposing jaw, shown as lower jaw (516). As shown in FIG. 22, the distance between inner perimeter (534) and outer perimeter (532) is generally uniform.

As shown in the top view of FIG. 22, each of body portion (520) and central void (536) have a generally oval shape when viewed from the top. Central void (536) is egg shaped and is wider adjacent proximal portion (524) than adjacent distal portion (526). Additionally, central void (536), which is formed by inner perimeter (534), forms a full oval (i.e. a 360-degree oval). Body portion (520) is oval shaped and forms about half oval (i.e. a 180-degree oval). Like FIG. 19 regarding distance (D3), the distance between outer perimeter (532) and inner perimeter (534) is generally uniform. Placement tip (514) includes a bend (538) disposed along a longitudinal axis (LA3) producing a bent oval shape for placement tip (514). As shown, placement tip (514) is generally formed from a rigid material. As shown in FIG. 22, placement tip (514) is symmetric about longitudinal axis (LA3). Alternatively, placement tip may be non-symmetric if desired. As shown in FIGS. 20A-20B, lower jaw (516) is thicker than anvil (518) that includes placement tip (514). Additionally, as shown in FIG. 22, lower jaw (516) is longer and wider than anvil (518) and placement tip (514).

In the present example, body portion (520) of placement tip (514) is integrally formed together with malleable member (522). As shown in FIG. 17, malleable member (522) includes first and second legs (540, 542) and a generally U-shaped portion (544) disposed within body portion (520). Malleable member (522) also includes a bent portion (548) shown in FIG. 23B. Malleable member (522) allows for ad hoc customization of the bend angle. As previously described, placement tip (514) may be removably coupled with or integrally formed with the anvil (518). As shown, distal end (552) of anvil (518) includes first and second coupling features (554, 556) that are configured to mate with first and second legs (540, 542) of malleable member (522).

In the present example, malleable member (522) is comprised of a malleable metal. Body portion (520) may be comprised of various metals, plastic, ceramic, combinations of metal with plastic or ceramic, and other suitable materials or combinations of materials that will be apparent to those of ordinary skill in the art in view of the teachings herein. Additionally, body portion (520) in some versions is entirely rigid, yet in other versions body portion (520) may be resilient to a lesser extent than malleable member (522). During the molding process, material flows through and fills mold surrounding malleable member (522). In this manner, malleable member (522) is securely connected with body portion (520) during the overmolding process. Alternatively, if less rigidity is desired, body portion (520), may comprise rubber, plastic, or any other suitable natural or synthetic material having the desired elastomeric properties.

Figure 23A:
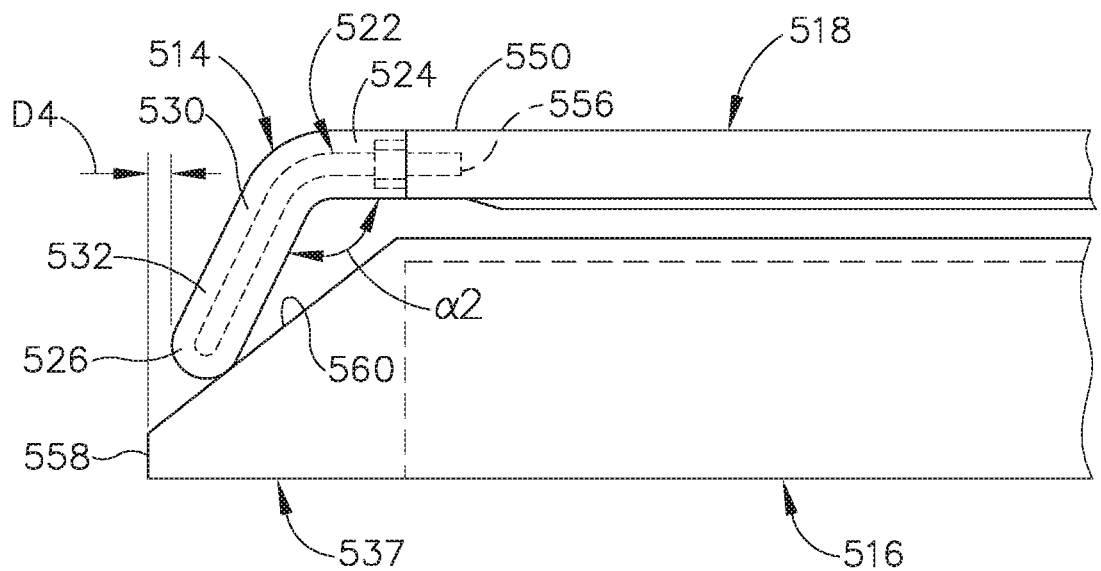
FIG. 23A depicts a side view of the end effector of FIG. 22 in a first bent configuration.
Figure 23B:
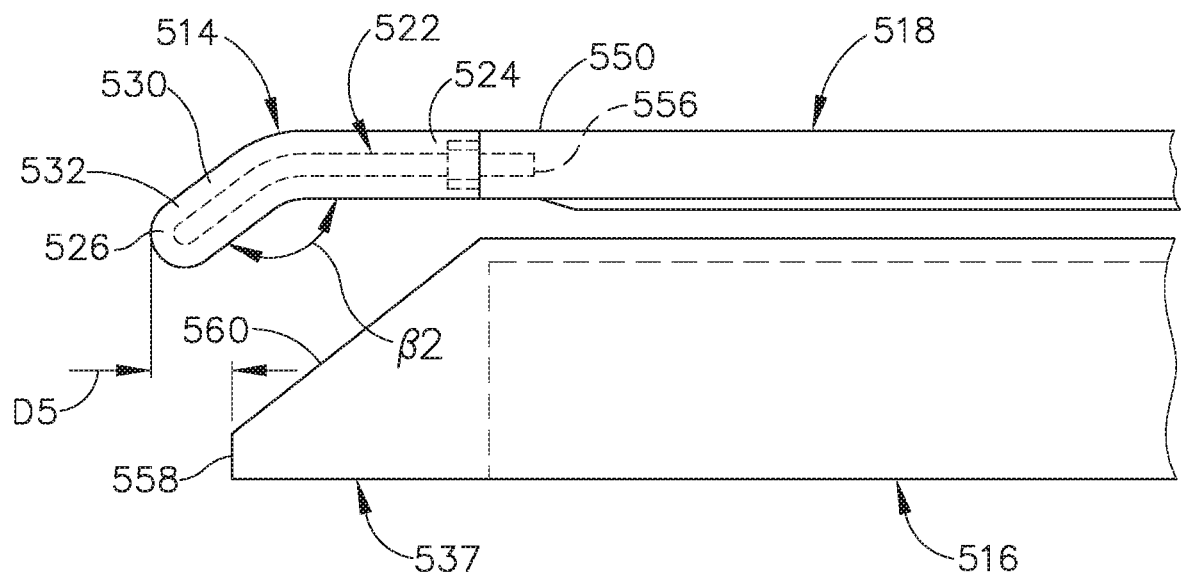
FIG. 23B depicts a side view of the end effector of FIG. 22 in a second bent configuration.

As shown in FIGS. 23A-23B, malleable member (522) is configured to increase the rigidity of placement tip (514) and allow an operator to customize the shape of placement tip (514) by producing different angles of placement tip (414). For example, FIG. 23A may refer to a pre-customized standard angle alpha ($\alpha 2$), while FIG. 23B may refer to a post-customized angle beta ($\beta 2$). As shown, angle alpha ($\alpha 2$), is less than angle beta ($\beta 2$). As shown in FIG. 23A in the pre-customized configuration, a distal end (558) of cartridge (537) extends a third distance (D4) beyond distal portion (526) of placement tip (514). Angled surface (560) of cartridge (537) is in contact with a distal portion (526) of placement tip (514). However, as shown in FIG. 23B in the post-customized configuration, distal portion (526) of placement tip (514) extends a fourth distance (D5) beyond distal end (558) of cartridge (537).

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An instrument, comprising: (a) a body; (b) a shaft extending from the body and defining a longitudinal axis; and (c) an end effector in communication with the shaft, wherein the end effector is operable to compress, staple, and cut tissue, wherein the end effector comprises: (i) first and second opposing jaws, wherein at least one of the first and second jaws is movable relative to the other of the first and second jaws between an open position and a closed position, (ii) a staple cartridge configured to hold one or more staples, wherein the staple cartridge is removably coupled with the second jaw, and (iii) a placement tip located at a distal end of the first jaw or a distal end of the second jaw, wherein the placement tip comprises: (A) first and second legs extending distally from one of the first or second jaws, wherein a void extends completely through the placement tip and separates the first and second legs, and (B) a distal portion that connects the first and second legs, wherein the distal portion has a first cross-sectional height that is greater than a second cross-sectional height of the first and second legs.

Example 2

The instrument of Example 1, wherein the first and second legs have a generally L-shaped cross-section.

Example 3

The instrument of any one or more of Examples 1 through 2, wherein the placement tip is formed from a generally rigid material, and wherein the void allows the placement tip to deflect relative to the opposite jaw.

Example 4

The instrument of any one or more of Examples 1 through 3, wherein the distal portion of the placement tip terminates at a sharp point, and wherein at least a portion on the distal portion is bent towards the opposing jaw.

Example 5

The instrument of any one or more of Examples 1 through 4, wherein the distal portion of the placement tip is rigid and is configured to jab at a small area of tissue and then dilate the small area by advancing the placement tip distally.

Example 6

The instrument of any one or more of Examples 1 through 5, wherein in the closed position, the distal portion is in contact with the opposite jaw and is configured to prevent the point of the distal portion from contacting tissue in the closed position.

Example 7

The instrument of any one or more of Examples 1 through 6, wherein the placement tip is integrally formed together as a unitary piece.

Example 8

The instrument of any one or more of Examples 1 through 7, wherein the placement tip is symmetric about the longitudinal axis.

Example 9

The instrument of any one or more of Examples 1 through 8, wherein the jaw opposite the placement tip is longer, wider, and thicker than the jaw including the placement tip.

Example 10

The instrument of any one or more of Examples 1 through 9, wherein the first and second legs each have a first width that is less than a second width of the void.

Example 11

An instrument, comprising: (a) a body; (b) a shaft extending from the body and defining a longitudinal axis; and (c) an end effector in communication with the shaft, wherein the end effector is operable to compress, staple, and cut tissue, wherein the end effector comprises: (i) first and second opposing jaws, wherein at least one of the first and second jaws is movable relative to the other of the first and second jaws between an open position and a closed position, (ii) a staple cartridge configured to hold one or more staples, wherein the staple cartridge is removably coupled with the second jaw, and (iii) a placement tip located at a distal end of the first jaw or a distal end of the second jaw, wherein the placement tip includes a body portion formed between an outer perimeter and an inner perimeter of the placement tip, wherein the inner perimeter is defined by a central void extending through the placement tip, and wherein at least a distal end of the body portion is bent towards the opposing jaw.

Example 12

The instrument of Example 11, wherein each of the body portion and the central void have a generally oval shape when viewed from the top, and wherein the placement tip includes a bend along the longitudinal axis producing a bent oval placement tip shape.

Example 13

The instrument of any one or more of Examples 11 through 12, further comprising a malleable member configured to increase the rigidity of the placement tip and configured to allow an operator to customize the shape of the placement tip by producing different placement tip angles.

Example 14

The instrument of any one or more of Examples 11 through 13, wherein the malleable member includes first and second legs and a generally U-shaped portion configured to contact the outer perimeter of the body portion.

Example 15

The instrument of any one or more of Examples 11 through 14, wherein the malleable member is integrally formed with the body portion between the inner and outer perimeters.

Example 16

The instrument of any one or more of Examples 11 through 14, wherein the malleable member is removably coupled with the placement tip.

Example 17

The instrument of any one or more of Examples 1 through 14 and 16, wherein the distal end of the first jaw or the distal end of the second jaw includes a coupling feature that is configured to mate with a coupling feature of the malleable member.

Example 18

The instrument of any one or more of Examples 1 through 14, 16, and 17, wherein the coupling feature of the malleable member includes a barbed fitting and the coupling feature at the distal end of the first jaw or the distal end of the second jaw includes a corresponding receptacle configured to securably couple with the barbed fitting.

Example 19

The instrument of any one or more of Examples 11 through 18, wherein the distance between the inner and outer perimeters is generally uniform.

Example 20

An instrument, comprising: (a) a body; (b) a shaft extending from the body and defining a longitudinal axis; and (c) an end effector in communication with the shaft, wherein the end effector is operable to compress, staple, and cut tissue, wherein the end effector comprises: (i) a first and second opposing jaws, wherein at least one of the first and second jaws is movable relative to the other of the first and second jaws between an open position and a closed position, (ii) a staple cartridge configured to hold one or more staples, wherein the staple cartridge is removably coupled with the second jaw, and (iii) a placement tip located at a distal end of the first jaw or a distal end of the second jaw, wherein the placement tip includes a central void extending therethrough, wherein the placement tip includes a malleable member configured to allow an operator to customize the shape of the placement tip by producing different placement tip angles.

Example 21

The instrument of Example 20, wherein the malleable member is removably coupled with the placement tip, and wherein the placement tip includes a barbed fitting and the receptible of the jaw includes a correspondingly shaped receptacle.

Example 22

The instrument of any one or more of Examples 20 through 21, wherein the body portion is integrally formed together as a unitary piece.

Example 23

The instrument of any one or more of Examples 20 through 22, wherein the jaw opposite the placement tip is longer, wider, and thicker than the jaw including the placement tip.

V. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should also be understood that the teachings herein may be readily combined with various teachings in U.S. patent application Ser. No. 16/035,865, entitled "Method of Surgical Stapling with End Effector Component Having a Curved Tip," filed on Jul. 16, 2018, published as U.S. Pub. No. 2018/0325516 on Nov. 15, 2018, the disclosure of which is incorporated by reference herein. Various suitable ways in which the teachings herein may be combined with the teachings of U.S. patent application Ser. No. 16/035,865, published as U.S. Pub. No. 2018/0325516 on Nov. 15, 2018, will be apparent to those of ordinary skill in the art.

It should also be understood that the teachings herein may be readily combined with various teachings in U.S. patent application Ser. No. 16/035,872, entitled "Permanent Attachment Means for Curved Tip of Component of Surgical Stapling Instrument," filed on Jul. 16, 2018, published as U.S. Pub. No. 2020/0015815 on Jan. 16, 2020, the disclosure of which is incorporated by reference herein. Various suitable ways in which the teachings herein may be combined with the teachings of U.S. patent application Ser. No. 16/035,872, published as U.S. Pub. No. 2020/0015815 on Jan. 16, 2020, will be apparent to those of ordinary skill in the art.

It should also be understood that the teachings herein may be readily combined with various teachings in U.S. patent application Ser. No. 16/035,821, entitled "Surgical Stapling End Effector Component with Deformable Tip Skewing in Multiple Planes," filed on Jul. 16, 2018, published as U.S. Pub. No. 2020/0015812 on Jan. 16, 2020, the disclosure of which is incorporated by reference herein. Various suitable ways in which the teachings herein may be combined with the teachings of U.S. patent application Ser. No. 16/035,821, published as U.S. Pub. No. 2020/0015812 on Jan. 16, 2020, will be apparent to those of ordinary skill in the art.

It should also be understood that the teachings herein may be readily combined with various teachings in U.S. patent application Ser. No. 16/035,825, entitled "Surgical Stapling End Effector Component with Articulation and Asymmetric Deformable Tip," filed on Jul. 16, 2018, published as U.S. Pub. No. 2020/0015813 on Jan. 16, 2020, the disclosure of which is incorporated by reference herein. Various suitable ways in which the teachings herein may be combined with the teachings of U.S. patent application Ser. No. 16/035,825, published as U.S. Pub. No. 2020/0015813 on Jan. 16, 2020, will be apparent to those of ordinary skill in the art.

It should also be understood that the teachings herein may be readily combined with various teachings in U.S. patent application Ser. No. 16/035,831, entitled "Surgical Stapling End Effector Component with Deformable Tip Having Thick Distal End," filed on Jul. 16, 2018, published as U.S. Pub. No. 2020/0015814 on Jan. 16, 2020, the disclosure of which is incorporated by reference herein. Various suitable ways in which the teachings herein may be combined with the teachings of U.S. patent application Ser. No. 16/035,831, published as U.S. Pub. No. 2020/0015814 on Jan. 16, 2020, will be apparent to those of ordinary skill in the art.

It should also be understood that the teachings herein may be readily combined with various teachings in U.S. patent application Ser. No. 16/035,834, entitled "Buttress Applier Cartridge for Surgical Stapler Having End Effector with Deflectable Curved Tip," filed on Jul. 16, 2018, published as U.S. Pub. No. 2020/0015817 on Jan. 16, 2020, the disclosure of which is incorporated by reference herein. Various suitable ways in which the teachings herein may be combined with the teachings of U.S. patent application Ser. No. 16/035,834, published as U.S. Pub. No. 2020/0015817 on Jan. 16, 2020, will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An instrument, comprising:
 (a) a body;
 (b) a shaft extending from the body and defining a longitudinal axis; and
 (c) an end effector in communication with the shaft, wherein the end effector is operable to compress, staple, and cut tissue, wherein the end effector comprises:
  (i) first and second opposing jaws, wherein at least one of the first and second jaws is movable relative to the other of the first and second jaws between an open position and a closed position,
  (ii) a staple cartridge configured to hold one or more staples, wherein the staple cartridge is removably coupled with the second jaw, and
  (iii) a placement tip located at a distal end of the first jaw or a distal end of the second jaw, wherein the placement tip comprises:
   (A) first and second leg portions extending distally from one of the first or second jaws, wherein a void extends completely through the placement tip and separates the first and second leg portions, wherein the void is defined by an inner perimeter that surrounds the void, and
   (B) a distal portion that connects the first and second leg portions, wherein the distal portion has a first cross-sectional height that is greater than a second cross-sectional height of the first and second leg portions, wherein the first cross-sectional height is taken parallel to the longitudinal axis and the second cross-sectional height is taken perpendicular to the longitudinal axis.

2. The instrument of claim 1, wherein the first and second leg portions have a L-shaped cross-section.

3. The instrument of claim 1, wherein the placement tip is formed from a stiff material, and wherein the void allows the placement tip to deflect relative to the opposite jaw.

4. The instrument of claim 1, wherein the distal portion of the placement tip terminates at a sharp point, and wherein at least a portion on the distal portion is bent towards the opposing jaw.

5. The instrument of claim 4, wherein the distal portion of the placement tip is stiff and is configured to jab at a small area of tissue and then dilate the small area by advancing the placement tip distally.

6. The instrument of claim 4, wherein in the closed position, the distal portion is in contact with the opposite jaw and is configured to prevent the point of the distal portion from contacting tissue in the closed position.

7. The instrument of claim 1, wherein the placement tip is integrally formed together as a unitary piece.

8. An instrument, comprising:
 (a) a body;
 (b) a shaft extending from the body and defining a longitudinal axis; and
 (c) an end effector in communication with the shaft, wherein the end effector is operable to compress, staple, and cut tissue, wherein the end effector comprises:
  (i) first and second opposing jaws, wherein at least one of the first and second jaws is movable relative to the other of the first and second jaws between an open position and a closed position,
  (ii) a staple cartridge configured to hold one or more staples, wherein the staple cartridge is removably coupled with the second jaw, and
  (iii) a placement tip located at a distal end of the first jaw or a distal end of the second jaw, wherein the placement tip includes a body portion formed between an outer perimeter and an inner perimeter of the placement tip, wherein the inner perimeter is defined by a void extending completely through the placement tip, wherein the inner perimeter extends 360 degrees about the void, and wherein at least a distal end of the body portion is bent towards the opposing jaw.

9. The instrument of claim 8, wherein each of the body portion and the void have a oval shape when viewed from the top, and wherein the placement tip includes a bend along the longitudinal axis producing a bent oval placement tip shape.

10. The instrument of claim 8, further comprising a malleable member configured to increase the stiffness of the placement tip and configured to allow an operator to customize the shape of the placement tip by producing different placement tip angles.

11. The instrument of claim 10, wherein the malleable member includes first and second leg portions and a U-shaped portion configured to contact the outer perimeter of the body portion.

12. The instrument of claim 10, wherein the malleable member is formed completely within the body portion between the inner and outer perimeters.

13. The instrument of claim 10, wherein the malleable member is removably coupled with the placement tip.

14. The instrument of claim 13, wherein the distal end of the first jaw or the distal end of the second jaw includes a coupling feature that is configured to mate with a coupling feature of the malleable member.

15. The instrument of claim 14, wherein the coupling feature of the malleable member includes a barbed fitting and the coupling feature at the distal end of the first jaw or the distal end of the second jaw includes a corresponding receptacle configured to securably couple with the barbed fitting.

16. The instrument of claim 8, wherein the distance between the inner and outer perimeters is uniform.

17. An instrument, comprising:
 (a) a body;
 (b) a shaft extending from the body and defining a longitudinal axis; and
 (c) an end effector in communication with the shaft, wherein the end effector is operable to compress, staple, and cut tissue, wherein the end effector comprises:
  (i) a first and second opposing jaws, wherein at least one of the first and second jaws is movable relative to the other of the first and second jaws between an open position and a closed position,
  (ii) a staple cartridge configured to hold one or more staples, wherein the staple cartridge is removably coupled with the second jaw, and (iii) a placement tip located at a distal end of the first jaw or a distal end of the second jaw, wherein the placement tip comprises:
   (A) a body portion, wherein the body portion includes a void extending therethrough, wherein the inner perimeter extends 360 degrees about the void, and
   (B) a malleable member configured to allow an operator to customize the shape of the placement tip by producing different placement tip angles.

18. The instrument of claim 17, wherein the malleable member is removably coupled with the body portion of the placement tip, and wherein the placement tip includes a barbed fitting and the receptible of the jaw includes a correspondingly shaped receptacle.

19. The instrument of claim 1, wherein at least one of the first and second jaws is pivotably rotatable relative to the other of the first and second jaws between the open position and the closed position.

20. The instrument of claim 8, wherein the inner perimeter extends along a majority of the length of the placement tip.

\* \* \* \* \*